US006841381B1

(12) United States Patent
Robinson et al.

(10) Patent No.: US 6,841,381 B1

(45) **Date of Patent: *Jan. 11, 2005**

(54) IMMUNIZATION BY INOCULATION OF DNA TRANSCRIPTION UNIT

(75) Inventors: Harriet L. Robinson, Southboro, MA (US); Ellen F. Fynan, Sterling, MA (US); Robert G. Webster, Memphis, TN (US); Shan Lu, Northboro, MA (US)

(73) Assignees: University of Massachusetts Medical Center, Worcester, MA (US); St. Jude Children's Research Hospital, Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/187,879

(22) Filed: Jan. 27, 1994

Related U.S. Application Data

(63) Continuation-in-part of application No. 08/009,833, filed on Jan. 27, 1993, now Pat. No. 5,643,578, which is a continuation-in-part of application No. 07/855,562, filed on Mar. 23, 1992, now abandoned.

(51) Int. Cl.[7] .......................... C12N 15/63; C12N 15/00

(52) U.S. Cl. .................. 435/320.1; 435/69.1; 435/325; 435/455

(58) Field of Search ............................ 514/44; 935/62; 424/199.1; 435/320.1, 325, 69.1, 455

(56) References Cited

U.S. PATENT DOCUMENTS

| | | | | |
|---|---|---|---|---|
| 4,722,848 A | | 2/1988 | Paoletti et al. | |
| 5,643,578 A | * | 7/1997 | Robinson et al. | 424/210.1 |
| 5,693,622 A | * | 12/1997 | Wolff et al. | 514/44 |
| 5,703,055 A | * | 12/1997 | Felgner et al. | 514/44 |

FOREIGN PATENT DOCUMENTS

| | | | |
|---|---|---|---|
| EP | 0292879 A3 | | 11/1988 |
| GB | 2166349 A | | 5/1986 |
| WO | WO 86/00930 | | 2/1986 |
| WO | WO 86/07593 | | 12/1986 |
| WO | WO89/07140 | | 8/1989 |
| WO | 8907140 | * | 8/1989 |
| WO | WO 90/02797 | | 3/1990 |
| WO | WO 90/02803 | | 3/1990 |
| WO | WO 90/11092 | | 10/1990 |
| WO | 9011092 | * | 10/1990 |
| WO | WO 92/01045 | | 1/1992 |
| WO | 9317706 | * | 9/1993 |
| WO | WO93/19183 | | 9/1993 |
| WO | WO 93/25235 | | 12/1993 |

OTHER PUBLICATIONS

Glaser, V. Biotech firms shift focus toward therapeutic HIV vaccine development. Genetic Engineering News, vol. 16, p. 6, Jan. 1996.*

Gilboa et al. Gene therapy for infectious diseases: the AIDS model. TIG, vol. 10, pp. 139–144, Apr. 1994.*

Cohen et al. HIV/AIDS in 1998–Gaining the upper hand? JAMA, vol. 280, pp. 87–88, Jul. 1998.*

Cheng et al. Virology 177: 816–819, 1990.*

Rekosh et al. PNAS 85:334–8, 1988.*

R. Weiss, Washington Post, p. A2, Apr. 30, 1997.*

R. Zinkernagel, in Fundamental Immunology, 3rd Ed., Ed. by W. Paul, Raven Press Ltd. NY, p. 1262, 1993.*

A. Hoffenbach, J. Immunology 142: 452–62, Jan. 15, 1989.*

L. Butini et al. Abstract, 1994.*

J. Kuby, Immunology, W.H. Freeman & Co., NY, 1992.*

F. Ledley, Hum. Gene Ther. 2:77–83, 1991.*

B. Haynes, Science vol. 260:1279–86, May 28, 1993.*

A. Townsend et al. Cell 39:13–25, Nov. 1984.*

Ulmer, JB et al; Heterologous Protection Against Influenza by Injection of DNA Encoding a Viral Protein; Science; 259:1745–1749 (1993).*

Tang, D et al; Genetic Immunization is a Simple Method for Eliciting an Immune Response; Nature; 356:152–154 (1992).*

Huylebroeck, D.; Viral Delivery Systems for Heterologous Antigens and Epitopes; Technological Advances in Vacc. Dev., 279–293 (1988).*

Haynes, B.F., Scientific and Social Issues of HIV Vaccine Development; Science; 260:1279–1286 (1993).*

Hoffenbach, A.; Unusually High Frequencies of HIV–Specific Cytotoxic T Lymphocytes in Humans; J. of Immun.; 142:452–462 (1989).*

Ledley, F.D; Clinical Considerations in the Design of Protocols for Somatic Gene Therapy; Human Gene Therapy; 2:77–83 (1991).*

Butini, L., et al; Comparative Analysis of HIV–specific CTL Activity in Lymphoid Tissue and Peripheral Blood; J. of Cell Biochem; 18B:147 (1994).*

Gardner, M.B., Simian and feline immunodeficiency viruses: animal lentivirus models for evaluation of AIDS vaccines and antiviral agents. *Antiviral Research 15*:267–286 (1991).

Gardner, M.D., "SIV Infection of Macques: A Model for Aids Vaccine Development." 21st Congress of the IABS, Annecy, France (1989).

Johnson, P.R., Hirsch, V.M., "SIV Infection of Macques as a Model for Aids Pathogenesis" *Intern. Rev. Immunol. 8*:55–63 (1992).

(List continued on next page.)

*Primary Examiner*—Dave T. Nguyen

(74) *Attorney, Agent, or Firm*—Fish & Richardson P.C.

(57) ABSTRACT

This invention relates to a method of immunizing a vertebrate, comprising introducing into the vertebrate a DNA transcription unit which comprises DNA encoding a desired antigen or antigens. The uptake of the DNA transcription unit by a host vertebrate results in the expression of the desired antigen or antigens, thereby eliciting humoral or cell-mediated immune responses or both humoral and cell-mediated responses. The elicited humoral and cell-mediated immune response can provide protection against infection by pathogenic agents, provide an anti-tumor response, or provide contraception. The host can be any vertebrate, avian or mammal, including humans.

10 Claims, 15 Drawing Sheets

OTHER PUBLICATIONS

McClure, H.M., et al., "Nonhuman Primate Models for Evaluation of AIDS Therapy" *Annals New York Academy of Sciences*.

Nable, G.J. and Felgner, PL., "Direct Gene Transfer For Immunotherapy and Immunization", *Trends in Biotechnology,* 11(5)211–215 (1993).

Barry, Michael A. et al., "Production of Monoclonal Antibodies by Genetic Immunization," *BioTechniques 16*(*4*):616–619 (1994).

Cox, Graham J.M. et al., "Bovine Herpesvirus 1: Immune Responses in Mice and Cattle Injected with Plasmid DNA," *Journal of Virology 67*(*9*):5664–5667 (1993).

Davis, Heather L. et al., "Direct Gene Transfer into Skeletal Muscle In Vivo: Factors Affecting Efficiency of Transfer and Stability of Expression," *Human Gene Therapy 4*:151–159 (1993).

Davis, Heather L. et al., "DNA–Based Immunization Induces Continuous Secretion of Hepatitis B Surface Antigen and High Levels of Circulating Antibody," *Human Molecular Genetics,* 2(11):1847–1851 (1993).

Davis, Heather L., et al., "Plasmid DNA Is Superior to Viral Vectors for Direct Gene Transfer into Adult Mouse Skeletal Muscle," *Human Gene Therapy 4,* 733–740 (1993).

Eisenbraun, Michael D. et al., "Examination of Parameters Affecting the Elicitation of Humoral Immune Responses by Particle Bombardment–Mediated Genetic Immunization," *DNA and Cell Biology 12*(*9*):791–797 (1993).

Fynan, Ellen F. et al., "DNA Vaccines: Protective Immunizations by Parenteral, Mucosal, and Gene–Gun Inoculations," *Proc. Natl. Acad. Sci. USA 90*: 11478–11482 (1993).

Fynan, E.F. et al., "Use of DNA Encoding Influenza Hemagglutinin as an Avian Influenza Vaccine," *DNA and Cell Biology 12*(*9*):785–789 (1993).

Montgomery, Donna L. et al., "Heterlogous and Homologous Protection Against Influenza A by DNA Vaccination: Optimization of DNA Vectors," *DNA and Cell Biology 12*(*9*):777–783 (1993).

Robinson, H.L., et al., "Protection Against a Lethal Influenza Virus Challenge by Immunization with a Haemagglutinin–Expressing Plasmid DNA," *Vaccine 11* (*9*):957–960 (1993).

Wang, Ban et al.,"DNA Inoculation Induces Neutralizing Immune Responses Against Human Immunodeficiency Virus Type 1 in Mice and Nonhuman Primates," *DNA and Cell Biology 12*(*9*):799–805 (1993).

Watanabe, Akira et al., "Induction of Antibodies to a κ V Region by Gene Immunization," *The Journal of Immunology 151*(*5*):2871–2876 (1993).

Yankauckas, Michelle A. et al., "Long–Term Anti–Nucleoprotein Cellular and Humoral Immunity Is Induced by Intramuscular Injection of Plasmid DNA Containing NP Gene," *DNA and Cell Biology 12*(*9*):771–776 (1993).

Brown, W. David, et al., "Assessment of Retrovirus–Expressed Nucleoprotein as a Vaccine against Lethal Influenza Virus Infections of Chickens," *Avian Diseases 36:* 515–520 (1992).

Parker, S.E. et al., "Intramuscular Vaccination of Plasmid DNA Containing Viral Antigens Provides Protection Against a Lethal Viral Challenge," Abstracts of papers presented at the 1992 meeting on Modern Approaches to New Vaccines including prevention of AIDS, Cold Spring Harbor Laboratory, New York, Sep. 16–20, 1992.

Rhodes, Gary H. et al., "Injection of Expression Vectors Containing Antigen Genes Induce Cellular and Humoral Immunity to the Antigen," Abstracts of papers presented at the 1992 meeting on Modern Approaches to New Vaccines including Prevention of AIDS, Cold Spring Harbor Laboratory, New York, Sep. 16–20, 1992.

Rhodes, Gary H. et al., "A Novel Method of Inducing Cellular and Humoral Immunity to HIV GP120 Protein by DNA Injection," Abstracts of papers presented at the 1992 meeting on Modern Approaches to New Vaccines including Prevention of AIDS, Cold Spring Harbor Laboratory, New York, Sep. 16–Sep. 20, 1992.

Liu, M.A. et al., "Immunization with DNA Encoding a Conserved Internal Viral Protein Results in Protection from Morbidity and Mortality Due to Challenge with Influenza A in Mice," abstracts of papers presented at the 1992 meeting on Modern Approaches to New Vaccines Including Prevention of AIDS, Cold Spring Harbor Laboratory, New York, Sep. 16–Sep. 20, 1992.

Wang, B. et al., "Genetic Immunization: A Novel Method for Vaccine Development Against HIV," Abstracts of papers presented at the 1992 meeting on Modern Approaches to New Vaccines Including Prevention of AIDS, Cold Spring Harbor Laboratory, New York, Sep. 16–20, 1992.

Tang, De–Chu et al., "Genetic Immunization is a Simple Method for Eliciting an Immune Response," *Nature 356:* 152–154 (1992).

Hunt, Lawrence, A. et al., "Retrovirus–Expressed Hemmagglutinin Protects against Lethal Influenza Virus Infections," *Journal of Virology 62* (*8*): 3014–3019 (1988).

Ulmer, Jeffrey B. et al., "Heterologous Protection Against Influenza by Injection of DNA Encoding a Viral Protein," *Science 259:* 1745–1749 (1993).

Webster, Robert G. et al., "Efficacy of Nucleoprotein and Haemagglutinin Antigens Expressed in Fowlpox Virus as Vaccine Influenza in Chickens," *Vaccine 9:* 303–308 (1991).

Wolff, Jon A. et al., "Direct Gene Transfer into Mouse Muscle in Vivo," *Science 247:* 1465–1468 (1990).

King, "Vical gene delivery technique may improve on HIV and other vaccines," *Biotechnology News 11*(*28*):5 (1991).

Huylebroeck, et al., "Viral delivery systems for Heterologous Antigens and Epitopes," *Technological Advances in Vaccine Development 84*:279–293 (1988).

Haynes et al., "Gene–gun–mediated DNA Immunization Elicits Humoral, Cytotoxic, and Protective Immune Responses," Vaccines, 94:65–70 (1994).

* cited by examiner

```
                        SEQUENCE LISTING


(1) GENERAL INFORMATION:

   (iii) NUMBER OF SEQUENCES: 19


(2) INFORMATION FOR SEQ ID NO:1:

     (i) SEQUENCE CHARACTERISTICS:
          (A) LENGTH: 43 base pairs
          (B) TYPE: nucleic acid
          (C) STRANDEDNESS: single
          (D) TOPOLOGY: linear

    (xi) SEQUENCE DESCRIPTION: SEQ ID NO:1:

GTCGCTCCTC TAGATTGTGG GTCACAGTCT ATTATGGGGT ACC                        43


(2) INFORMATION FOR SEQ ID NO:2:

     (i) SEQUENCE CHARACTERISTICS:
          (A) LENGTH: 35 base pairs
          (B) TYPE: nucleic acid
          (C) STRANDEDNESS: single
          (D) TOPOLOGY: linear

    (xi) SEQUENCE DESCRIPTION: SEQ ID NO:2:

GGTCGGATCC TTACTGCACC ACTCTTCTCT TTGCC                                 35


(2) INFORMATION FOR SEQ ID NO:3:
```

-continued (i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:3:

CGACGGATCC TTATGTTATG TCAAACCAAT TCCAC 35

(2) INFORMATION FOR SEQ ID NO:4:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO:4:

```
Arg Ile Gln Arg Gly Pro Gly Arg Ala Phe Val Thr Ile Gly Lys
1               5                   10                  15
```

(2) INFORMATION FOR SEQ ID NO:5:

(i) SEQUENCE CHARACTERISTICS:
(A) LENGTH: 34 amino acids
(B) TYPE: amino acid
(C) STRANDEDNESS: single
(D) TOPOLOGY: linear (xi) SEQUENCE DESCRIPTION: SEQ ID NO:5:

```
Cys Thr Arg Pro Asn Tyr Thr Thr Arg Lys Arg Ile His Ile Gly Pro
1               5                   10                  15

Gly Arg Ala Phe Tyr Thr Thr Lys Asn Ile Ile Gly Asn Ile Lys Gln
            20                  25                  30

Ala His
```

(2) INFORMATION FOR SEQ ID NO:6:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:6:

```
Cys Thr Arg Pro Asn Tyr Lys Thr Arg Ser Arg Ile His Ile Gly Pro
1               5                   10                  15

Gly Arg Ala Phe Tyr Thr Thr Lys Asn Ile Arg Gly Asp Ile Arg Gln
            20                  25                  30

Ala His Cys
        35
```

(2) INFORMATION FOR SEQ ID NO:7:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:7:

```
Cys Thr Arg Pro Asn Tyr Lys Thr Arg Ser Arg Ile His Ile Gly Pro
1               5                   10                  15

Gly Arg
```

-continued (2) INFORMATION FOR SEQ ID NO:8:

(i) SEQUENCE CHARACTERISTICS:
(A) LENGTH: 22 amino acids
(B) TYPE: amino acid
(C) STRANDEDNESS: single
(D) TOPOLOGY: linear (xi) SEQUENCE DESCRIPTION: SEQ ID NO:8:

```
Cys Thr Arg Pro Asn Tyr Lys Thr Ser Arg Arg Ile His Ile Gly Pro
1               5                   10                  15

Gly Arg Ser Phe Tyr Thr
            20
```

(2) INFORMATION FOR SEQ ID NO:9:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:9:

```
Cys Thr Arg Pro Asn Asn Asn Thr Arg Lys Ser Ile His Ile Gly Pro
1               5                   10                  15

Gly Arg Ala Ile Tyr Thr Thr Gly Gln Ile Ile Gly Asp Ile Arg Gln
            20                  25                  30

Ala His Cys
        35
```

(2) INFORMATION FOR SEQ ID NO:10:

(i) SEQUENCE CHARACTERISTICS:
(A) LENGTH: 23 amino acids
(B) TYPE: amino acid
(C) STRANDEDNESS: single
(D) TOPOLOGY: linear (xi) SEQUENCE DESCRIPTION: SEQ ID NO:10:

```
Cys Thr Arg Pro Asn Asn Asn Thr Arg Lys Ser Ile His Ile Gly Pro
1               5                   10                  15

Gly Arg Ala Ile Tyr Thr Thr
            20
```

(2) INFORMATION FOR SEQ ID NO:11:

(i) SEQUENCE CHARACTERISTICS:
(A) LENGTH: 30 amino acids
(B) TYPE: amino acid
(C) STRANDEDNESS: single
(D) TOPOLOGY: linear (xi) SEQUENCE DESCRIPTION: SEQ ID NO:11:

```
Cys Thr Arg Pro Asn Asn Asn Thr Arg Lys Ser Ile His Ile Gly Pro
1               5                   10                  15

Gly Arg Ala Phe Tyr Thr Thr Ala Ile Ile Gly Asp Ile Arg
            20                  25                  30
```

(2) INFORMATION FOR SEQ ID NO:12:

(i) SEQUENCE CHARACTERISTICS:
(A) LENGTH: 35 amino acids
(B) TYPE: amino acid
(C) STRANDEDNESS: single -continued (D) TOPOLOGY: linear (xi) SEQUENCE DESCRIPTION: SEQ ID NO:12:

Cys Thr Arg Pro Asn Asn Asn Thr Arg Arg Arg Ile His Ile Gly Pro
1 5 10 15

Gly Arg Ala Ile Tyr Thr Thr Gly Gln Ile Ile Gly Asp Ile Arg Gln
20 25 30

Ala His Cys
35

(2) INFORMATION FOR SEQ ID NO:13:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:13:

Cys Thr Arg Pro Asn Asn Asn Thr Arg Arg Arg Ile His Ile Gly Pro
1 5 10 15

Gly Arg Ala Ile Tyr Thr Thr Gly Gln Ile Ile Gly Asp Ile Arg Gln
20 25 30

Ala His Cys
35

(2) INFORMATION FOR SEQ ID NO:14:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:14:

Cys Thr Arg Pro Asn Asn Asn Thr Arg Arg Arg Ile His Ile Gly Pro
1 5 10 15

Gly Arg Ala Ile Tyr Thr Thr Gly Gln Ile Ile Gly Asp Ile Arg Gln
20 25 30

Ala His Cys
35

(2) INFORMATION FOR SEQ ID NO:15:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO:15:

Cys Thr Arg Pro Asn Asn Asn Thr Arg Arg Arg Ile His Ile Gly Pro
1 5 10 15

Gly Arg Ala (2) INFORMATION FOR SEQ ID NO:16:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:16:

-continued

```
Cys Thr Arg Pro Asn Asn Asn Thr Arg Arg Arg Ile His Ile Gly Pro
1               5                   10                  15

Gly Arg Ala Ile Tyr Thr Thr Gly Gln Ile Ile Gly Asp Ile Arg Gln
            20                  25                  30

Ala His Cys
        35
```

(2) INFORMATION FOR SEQ ID NO:17:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:17:

```
Cys Thr Arg Pro Asn Asn Asn Thr Arg Arg Arg Ile His Ile Gly Pro
1               5                   10                  15

Gly Arg Ala Ile Tyr Thr Thr Gly Gln Ile Ile Gly Asp Ile Arg Gln
            20                  25                  30

Ala His Cys
        35
```

(2) INFORMATION FOR SEQ ID NO:18:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO:18:

```
Cys Thr Arg Pro Asn Asn Asn Thr Arg Arg Arg Ile His Ile Gly Pro
1               5                   10                  15

Gly Arg Ala
```

(2) INFORMATION FOR SEQ ID NO:19:

(i) SEQUENCE CHARACTERISTICS:
(A) LENGTH: 35 amino acids
(B) TYPE: amino acid
(C) STRANDEDNESS: single
(D) TOPOLOGY: linear (xi) SEQUENCE DESCRIPTION: SEQ ID NO:19:

```
Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35
```

IMMUNIZATION BY INOCULATION OF DNA TRANSCRIPTION UNIT

RELATED APPLICATION

This Application is a Continuation-in-Part of U.S. application Ser. No. 08/009,833, filed Jan. 27, 1993, now U.S. Pat. No. 5,643,578, which is a Continuation-in-Part of U.S. application Ser. No. 07/855,562 filed Mar. 23, 1992, now abandoned. The teachings of these applications are incorporated herein by reference.

GOVERNMENT SUPPORT

Work described herein was supported by U.S. Public Health Service Grants, Number RO1 CA 23086 and Number RO1 A1 08831. The U.S. Government has certain rights in this invention.

BACKGROUND OF THE INVENTION

Vaccination with inactivated or attenuated organisms or their products has been shown to be an effective method for increasing host resistance and ultimately has led to the eradication of certain common and serious infectious diseases. The use of vaccines is based on the stimulation of specific immune responses within a host or the transfer of preformed antibodies. The prevention of certain diseases, such as poliomyelitis, by vaccines represents one of immunology's greatest triumphs.

Effective vaccines have been developed for relatively few of the infectious agents that cause disease in domestic animals and man. This reflects technical problems associated with the growth and attenuation of virulent strains of pathogens. Recently effort has been placed on the development of subunit vaccines (vaccines that present only selected antigens from a pathogen to the host). Subunit vaccines have the potential for achieving high levels of protection in the virtual absence of side effects. Subunit vaccines also offer the opportunity for the development of vaccines that are stable, easy to administer, and sufficiently cost-effective for widespread distribution.

SUMMARY OF THE INVENTION

This invention relates to a method of subunit vaccination. Specifically, this invention relates to a method of immunizing an individual, comprising introducing into the individual a DNA transcription unit (or units) which comprises DNA encoding a desired antigen or antigens and DNA encoding a transcriptional promoter element or elements. A single transcription unit or multiple DNA transcription units can be administered to an individual to achieve immunization against one antigen or multiple antigens. The uptake of the DNA transcription units by host cells results in the expression of the desired antigen or antigens, thereby eliciting humoral or cell-mediated immune responses or both humoral and cell-mediated responses. The elicited humoral and cell-mediated immune response can provide protection against infection by pathogenic agents, provide an anti-tumor response, or provide contraception. The host can be any vertebrate, avian or mammalian, including humans.

The present invention relates to the use of DNA transcription units for raising immune responses. In one embodiment, the individual is immunized by parenteral routes of inoculation. These include intravenous, intramuscular, intradermal, and subcutaneous administration of DNA transcription units. DNAs administered to the skin can be delivered with a DNA gun. In a second embodiment, the individual is immunized by contacting a mucosal surface, such as a respiratory mucosal surface, with DNA transcription units in such a manner that the transcription units are taken up by (i.e., enter the cells of) the mucosal surface. DNAs for mucosal administration can be microsphere encapsulated.

The DNA transcription units introduced by the present method can be used to express any antigen encoded by an infectious agent, such as a virus, a bacterium, a fungus, or a parasite, as well as antigenic fragments and peptides that have been experimentally determined to be effective in immunizing an individual against infection by a pathogenic agent. As stated above, DNA transcription units can also be used for contraceptive purposes or for anti-cancer therapy.

The desired antigens to be expressed can be designed so as to give internal, surface, secreted, or budding and assembled forms of the antigens being used as immunogens.

There are numerous advantages of the use of DNA for immunizations. For example, immunization can be accomplished for any antigen encoded by DNA. Furthermore, the DNA encoded antigens are expressed as "pure" antigens in their native states and have undergone normal host cell modifications. Also, DNA is easily and inexpensively manipulated and is stable as a dry product or in solution over a wide range of temperatures. Thus, this technology is valuable for the development of highly effective subunit vaccines.

DETAILED DESCRIPTION OF THE INVENTION

Figure 1:
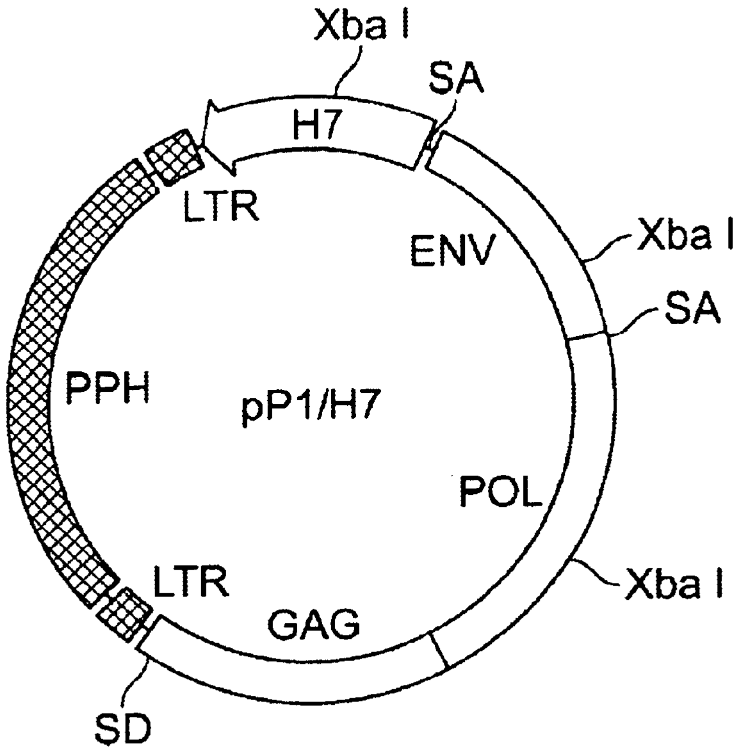
FIG. 1 is a schematic representation of a bacterial plasmid containing a DNA transcription unit (referred to as pP1/H7) comprising an influenza virus hemagglutinin type 7 (H7) gene expressed by a replication competent retroviral vector.

This invention relates to a method of immunizing vertebrates, particularly mammals, including humans, against a protein, a pathogen, or an infectious agent, thereby eliciting humoral and/or cell-mediated immune responses which interfere with the activity of the protein, or which limit the spread or growth of the infectious agent and result in protection against subsequent challenge by the pathogen or infectious agent. In the method of the present invention, a DNA transcription unit is administered to an individual in whom immunization is desired.

The term "immunizing" refers herein to the production of an immune response in a vertebrate which protects (partially or totally) from the manifestations of infection (i.e., disease) caused by an infectious agent. That is, a vertebrate immunized by the present invention will not be infected or will be infected to a lesser extent than would occur without immunization.

A DNA transcription unit is a polynucleotide sequence, bounded by an initiation site and termination site, that is transcribed to produce a primary transcript. As used herein, a "DNA transcription unit" includes at least two components: antigen-encoding DNA and transcriptional promoter element or elements. Antigen-encoding DNA can encode one antigen or multiple antigens, such as multiple HIV antigens or antigens from two or more different proteins or infectious agents. The DNA transcription unit can additionally be inserted into a vector which includes sequences for replication of the DNA transcription unit. A DNA transcription unit can optionally include additional sequences, such as: enhancer elements, splicing signals, termination and polyadenylation signals, viral replicons and bacterial plasmid sequences. In the present method, a DNA transcription unit (i.e., one type of transcription unit) can be administered, or a combination of two or more types of DNA transcription units can be administered.

The DNA transcription unit can be produced by a number of known methods. For example, using known methods, DNA encoding the desired antigen can be inserted into an expression vector. See Maniatis et al., *Molecular Cloning, A Laboratory Manual*, 2d, Cold Spring Harbor Laboratory Press (1989).

The DNA transcription unit can be administered to an individual, or inoculated, in the presence of adjuvants or other substances that have the capability of promoting DNA uptake or recruiting immune system cells to the site of the inoculation. It should be understood that the DNA transcription unit itself is expressed in the host cell by transcription factors provided by the host cell, or provided by a DNA transcriptional unit.

The "desired antigen" can be any antigen or combination of antigens expressed by an infectious agent, or any antigen or combination of antigens that has been determined to be capable of eliciting a protective response. The desired antigen can also be a tumor antigen or an antigen which provides protection against conception. The antigen or antigens can be naturally occurring, or can be mutated or specially modified. The antigen or antigens can represent different forms, such as subgroups (clades), subtypes or serotypes of an infectious agent. These antigens may or may not be structural components of a cell or an infectious agent. The encoded antigens can be translation products or polypeptides. The polypeptides can be of various lengths. They can undergo normal host cell modifications such as glycosylation, myristoylation or phosphorylation. In addition, they can be designed to undergo intracellular, extracellular or cell-surface expression. Furthermore, they can be designed to undergo assembly and release from cells.

Potential pathogens for which the DNA transcription unit can be used include DNA encoding antigens derived from any virus, chlamydia, mycoplasma, bacteria, parasite or fungi. Viruses include the herpesviruses, orthomyxoviruses, rhinoviruses, picornaviruses, adenoviruses, paramyxoviruses, coronaviruses, rhabdoviruses, togaviruses, flaviviruses, bunyaviruses, rubella virus, reovirus, hepadna viruses and retroviruses including simian immunodeficiency virus or human immunodeficiency virus. Bacteria include mycobacteria, spirochetes, rickettsias, chlamydia, and mycoplasma. Fungi include yeasts and molds. Parasites include malaria. It is to be understood that this list does not include all potential pathogens against which a protective immune response can be generated according to the methods herein described.

An individual can be inoculated through any parenteral route. For example, an individual can be inoculated by intravenous, intraperitoneal, intradermal, subcutaneous or intramuscular methods, or by the gene gun. An individual can be inoculated by any mucosal route. The DNA transcription unit can be administered to a mucosal surface by a variety of methods, including DNA-containing nose-drops, inhalants, suppositories or by microsphere encapsulated DNA. For example, the DNA transcription unit can be administered to a respiratory mucosal surface, such as the nares or the trachea.

Any appropriate physiologically compatible medium, such as saline, is suitable for introducing the DNA transcription unit into an individual.

Immunization as described herein was accomplished with various DNA transcription units (e.g., vectors) that express different proteins. The DNA transcription units described herein are representative of the types of transcription units that can be used in the current invention. The DNA transcription units can encode antigens from a single infectious agent, including antigens from different subgroups (clades) or subtypes of the infectious agent, and can additionally encode antigens from more than one infectious agent.

In one embodiment of the current invention, immunization was accomplished using a DNA transcription unit encoding the murine rotavirus neutralization capsid protein VP7. In another embodiment, influenza virus hemagglutinin glycoproteins were used. The hemagglutinin glycoprotein mediates adsorption and penetration of virus and is a major target for neutralizing antibodies. Influenza virus hemagglutinin proteins have 14 different serological subtypes. In a particular embodiment, DNA expression vectors for the H7 subtype (comprising a DNA transcription unit encoding the H7 subtype hemagglutinin) have been used to provide protection against challenge with an H7N7 virus in an avian model. In another particular embodiment, a DNA transcription unit expressing the H1 hemagglutinin has been used to immunize against an H1N1 virus in a murine model. A mixture of DNA transcription units, comprising DNA encoding a variety of antigens from different subgroups (e.g., A and B) and/or from different subtypes (such as subtypes 1–14 of subgroup A) of influenza, can also be used in the current invention.

In addition, experiments have been conducted to examine the immunogenicity of human immunodeficiency virus (HIV-1) and simian immunodeficiency virus ($SIV_{mac}$) DNA transcription units in mice and monkeys. DNA vaccines for immunodeficiency virus are designed to raise broad cell-mediated as well as humoral responses. This is accomplished by using a mix of DNAs encoding different HIV antigens. This mix can include two main components. The first, termed dpol constructs, serve to raise cytotoxic T-cell responses against a wide variety of HIV-1 proteins. The second, termed Env constructs, serve to raise antibody responses against the spectrum of Envs present in endemic infections.

The dpol DNA constructs encode a non-infectious DNA, because one of the nine proteins is not included in the construct. The constructs mimic many of the characteristics of a live infection. Attenuation can be accomplished by a number of mutations. One example includes rendering the long terminal repeats (LTRs) non-functional by point mutations, deletions or truncations and rendering the polymerase gene non-functional by point mutations or internal deletions. Altered expression of other genes is optional. Thus, these constructs give the opportunity for expressing 8 out of 9 HIV-1 proteins (Gag, Env, Vif, Vpr, Vpu, Tat, Rev and Nef) or 8 out of 9 $SIV_{mac}$ proteins (Gag, Env, Vif, Vpr, Vpx, Tat, Rev and Nef). Expression of this extensive repertoire of HIV-1 or $SIV_{mac}$ proteins facilitates the activation of the cytotoxic arm of the immune system in individuals of diverse histocompatibility types. The number of epitopes expressed increases the chance that epitopes are present that can be recognized by individual histocompatibility types. Each histocompatibility type will presumably recognize and present a subset of the expressed epitopes.

The dpol constructs also facilitate the raising of CTL responses that are directed against regulatory as well as structural HIV-1 proteins. The expression of the regulatory proteins by the dpol DNAs affords the opportunity for raising cytotoxic responses against the proteins which are expressed earliest in infections and which are most active in latent infections. This offers the vaccinated host the possibility of clearing cells before they have produced virus. It also affords the opportunity of clearing cells that have latent infections.

A mix of Env constructs is used in conjunction with the dpol constructs to raise a broad antibody response against Env. A broad humoral response to Env is important because Env is the protein which is exposed on extracellular virus. Thus antibodies to Env can prevent infection by processes such as neutralization and complement mediated lysis. A broad response to Env is important because Env is the HIV-1 protein which undergoes the most marked evolution in infected humans. The mix of Envs can include:

(1) Envs that represent different subgroups of HIV-1, such as subgroups A to F. These are used to provide broad geographic protection (Myers et al., Human Retroviruses and AIDS, Los Alamos National Laboratory, Los Alamos N.Mex. (1992)).

(2) Envs from within a subgroup that represent growth characteristics representative of different phases of infection or or have distinct tissue tropisms. These are used to provide protection against the spectrum of viruses present in an endemic infection.

(3) Envs representative of those favored for different routes of transmission. These include Envs representative of homosexual transmission, heterosexual transmission, transmission by intravenous drug use, trans-placental transmission or neonatal transmission.

(4) Mutant forms of env that may be particularly effective at raising desired immune responses. An example of such an env is the HXB-2 Env that has been deleted for V1, V2 and V3 sequences by Dr. Joseph Sodroski (Dana Farber Cancer Institute, Boston, Mass.). This Env retains the conformational epitopes associated with the CD4 binding domain and may be particularly effective in raising antibody that will have broad neutralizing activity (Wyatt, et al., 1993, *J. Virol.* 67:4557–4565).

Different structural forms of Env are expressed by the DNAs used in vaccines. These forms can include a soluble form of gp120, such as sgp120. This form is particularly effective at raising antibody to V3 loop determinants (Earl et al., 1994, *J. Virol.* in press). A second form which can be expressed is a soluble form of gp140, such as sgp140. This form represents an oligomer of the extracellular components of Env; it raises antibody against gp41 as well as antibody against gp120, and also raises antibodies that recognize oligomeric forms of Env that are present in the assembled envelope spikes found on virions (Earl et al., *J. Virol.*, in press; Moore, et al., *J. Virol.* 68:469–484 (1994)). The sgp120 and sgp140 are released from cells, facilitating their entry into major histocompatibility class II-dependent pathways of antigen presentation and the raising of T-cell dependent B-cell responses. A native form of Env (gp160) can also be expressed. This membrane-anchored form of Env represents the form of Env found on the surfaces of virions and infected cells.

The following Examples describe vaccination trials using direct DNA inoculations designed for use in influenza virus, rotavirus, and immunodeficiency virus models. Vaccination trials for influenza virus use avian, murine, and ferret models. The avian and murine models demonstrate protective immunizations against lethal challenges, wherein challenge of an unimmunized animal caused death. The ferret model demonstrated protective immunizations against virus replication in the nares; challenge of an unimmunized animal resulted in virus replication in the nares. Vaccination trials for rotavirus used a murine model. The murine model demonstrated antibody and cytotoxic T-cell activity in animals receiving DNA transcriptional units for rotavirus protein, wherein animals receiving control DNA exhibited no antibody or cytotoxic T-cell activity for rotavirus. Vaccination trials for immunodeficiency virus used murine and simian models. The murine model demonstrated antibody including neutralizing antibody and cytotoxic T-cell activity in animals receiving DNA transcriptional units for human immunodeficiency virus type 1 (HIV-1), wherein animals receiving control DNA exhibited no antibody or cytotoxic T-cell activity. The simian model is used to test for the raising of responses that will protect against a lethal challenge with simian immunodeficiency virus-macaque ($SIV_{mac}$).

The current invention is illustrated by the following examples, which are not to be construed as limiting in any way.

EXAMPLE 1

Immunization of Chickens Against Influenza Virus

Figure 2:
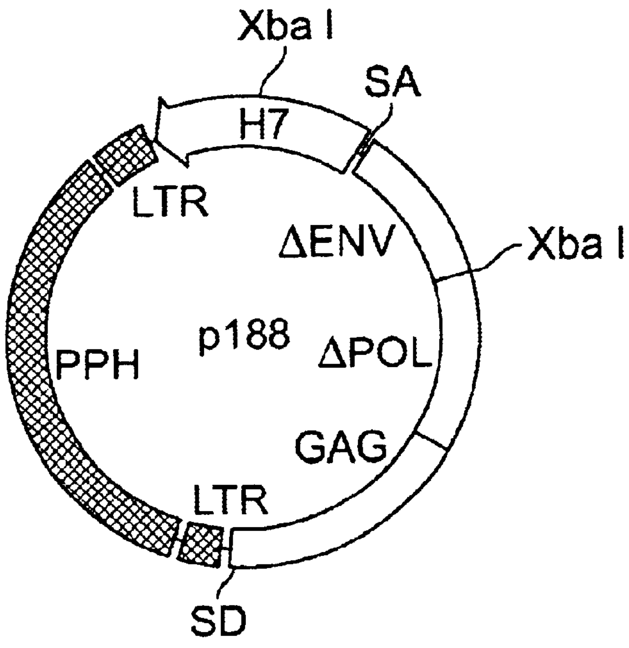
FIG. 2 is a schematic representation of a bacterial plasmid containing a DNA transcription unit (p188) comprising an influenza virus hemagglutinin type 7 (H7) gene expressed by a replication defective retroviral vector.
Figure 3:
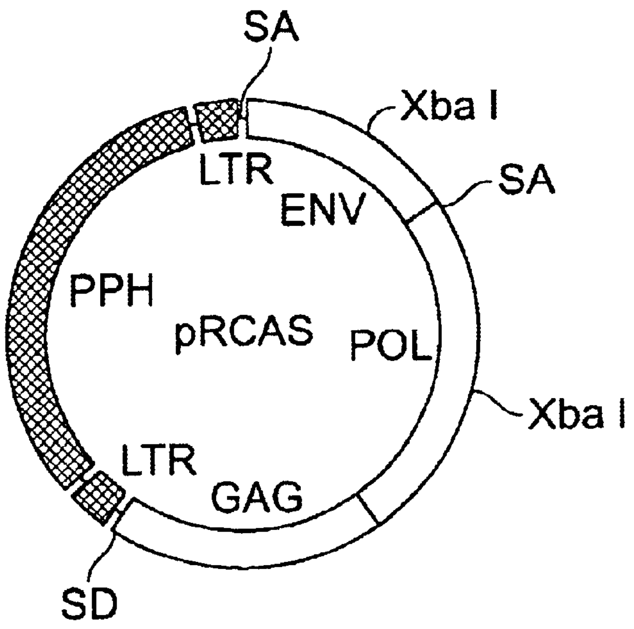
FIG. 3 is a schematic representation of a bacterial plasmid comprising a retroviral vector (pRCAS) with no H7 insert, used as a control.

A DNA transcription unit referred to as pP1/H7 (FIG. 1), encoding a replication competent avian leukosis virus expressing the influenza virus hemagglutinin type 7 (H7) gene was constructed as described in Hunt et al., *J. of Virology*, 62(8):3014–3019 (1988). DNA unit p188 (FIG. 2) encoding a replication defective derivative of pP1/H7 that expresses H7 but is defective for the avian virus vector polymerase and envelope proteins was constructed by deleting an XbaI fragment from pP1/H7. DNA unit pRCAS (FIG. 3), encoding the avian leukosis virus vector, with no influenza virus insert, was constructed as described in Hughes et al., *J. of Virology*, 61:3004 (1987). DNA units were diluted in saline at a concentration of 100 μg per 0.2 ml for inoculation.

To test the ability of the inoculated DNA to protect against a lethal influenza virus challenge, groups of three-week old chicks were inoculated with pP1/H7, p188, or pRCAS DNA. Specific pathogen free chicks that are maintained as an avian-leukosis virus-free flock (SPAFAS, Norwich, Conn.) were used for inoculations. Each chick received 100 μg of DNA intravenously (iv), 100 μg intraperitoneally (ip), and 100 μg subcutaneously (sc). Four weeks later, chicks were bled and boosted with 300 μg of DNA (100 μg iv, 100 μg ip, and 100 μg sc). At one week post-boost, chicks were bled and challenged by the nares with 100 lethal $doses_{50}$ ($1\times10^4$ egg infectious doses) of a highly pathogenic type H7 avian influenza virus, A/Chicken/Victoria/1/85 (H7N7) (Ck/Vic/85). The H7 gene of Ck/Vic/85 differs in about 15% of its codons from that of the immunizing H7 (Hunt et al., *J. of Virology* 62(6):3014–3019 (1988)). Thus, the Ck/Vic/85 challenge tests for the ability to achieve broad cross-protection within the H7 subtype. Ck/Vic/85 spreads rapidly throughout the internal organs and brain of chickens, causing death within 4–7 days. Post-challenge, the chickens were observed daily for ten days for signs of disease. One and one half weeks after challenge, sera were obtained from surviving birds. These as well as the pre- and post-boost sera were used for analyses for anti-H7 antibodies (See below).

TABLE 1

Protection Against Lethal H7N7 Influenza Virus with DNA Coding for H7 Hemagglutinin

| Group | # Survivors/ # Tested | HI TITERS Post-vaccine 4 weeks | Post-boost 1 week | Post-Challenge 1.5 weeks |
|---|---|---|---|---|
| pP1/H7 | 6/6 | <.[a] | <. | 864 (160–1280) |
| p188 | 6/6 | <[b] | < | 427 (160–1280) |
| pRCAS | 0/6 | < | < | +[c] |

[a](<.) means one of six birds had an HI titer of 10.
[b](<) means that all birds had titers of less than 10.
[c](+) means that all birds died.

The H7-expressing DNA transcription units protected each of the chickens inoculated with pP1/H7 or p188 (Table 1). In contrast, inoculation with the control DNA, pRCAS, failed to protect the chickens against lethal virus challenge. The birds in the control group started to show signs of disease on the second day post-challenge. By the third day, three of the six control birds had died and all control birds were dead by the fifth day. The birds inoculated with hemagglutinin-expressing DNAs showed no signs of disease. By one and one half weeks post challenge both of these groups had developed high levels of HI antibody.

Additional Experiments

To assess the reproducibility of the protection elicited by immunization with the replication-defective H7-expressing DNA, the experiment described above was repeated three times using only p188 and pRCAS DNAs for inoculations, with the difference that the chicks were challenged two weeks post-boost instead of one week post-boost as in the first experiment. Three-week-old SPAFAS chicks were inoculated with 100 μg of DNA by each of three routes (iv, ip and sc). Four weeks later, they were boosted by inoculation with 100 μg of DNA administered iv, ip and sc. Two weeks later, chickens were challenged via the nares with 100 lethal $doses_{50}$ of Ck/Vic/85 (H7N7).

The results of the repeat experiments confirmed that the H7-expressing p188 DNA could afford protection against a lethal challenge, as shown in Table 2.

TABLE 2

Reproducibility of Protection Against a Lethal H7 Virus Challenge by Immunization with p188 DNA[a]

| Expt. | Fate of Challenge Group (# survivors/# tested) p188 DNA | pRCAS DNA | Amantadine | No treatment |
|---|---|---|---|---|
| 1 | 6/6 | 0/6 | — | — |
| 2 | 5/6 | 1/5 | 4/5 | — |
| 3 | 9/32 | 0/32 | — | — |
| 4 | 8/12 | 0/12 | — | 0/12 |
| Total | 28/56 | 1/55 | 4/5 | 0/12 |

[a]Experiment 1 is the same as that presented in Table 1.
—, not tested.

In contrast to the first experiment, in which all of the p188-inoculated chickens survived the lethal challenge, immunizations in the second, third, and fourth experiments resulted in protection in 28% to 83% of the vaccinated birds. Further, in contrast to the first experiment in which vaccinated birds showed no signs of disease, most of the survivors of the repeat experiments showed transient signs of post-challenge sickness. As in the first experiment, the control DNA did not provide protection. Summing the results of the four experiments, 28 out of 56 p188-vaccinated birds survived; only one of 55 control birds survived. Thus, highly significant protection was achieved. This level of protection is particularly impressive in view of the fact that immunizing and challenge H7 genes had undergone antigenic drift of about 15% in the amino acid sequence.

EXAMPLE 2

Analysis of Antibody Response to H7 in Vaccinated and Unvaccinated Animals

To allow the comparison of antibody responses to H7 in vaccinated and unvaccinated chickens, Experiment 2 from Example 1 (see Table 2) included a non-vaccinated group rescued with the anti-influenza A virus drug, amantadine-HCL (Webster, R. G., et al., *J. Virol.* 55:173–176 (1985)). All of the five amantadine-treated birds developed disease. Four of these survived, providing sera that could be used to compare antibody responses to H7 in immunized and non-immunized chickens.

Sera from p188 inoculated and amantadine-treated birds in the second experiment were analyzed for the time course of antibody responses to H7 and to other influenza virus proteins. Antibody responses to H7 were quantitated using hemagglutination inhibition (HI) as well as virus neutralization and enzyme-linked immunosorbent assays (ELISA). In tests for hemagglutination inhibition, sera were analyzed in microtiter plates with receptor-destroying enzyme-treated sera as described by Palmer et al., *Advanced Laboratory Techniques for Influenza Diagnosis*, p. 51–52, Immunology series no. 6, U.S. Department of Health, Education, and Welfare, Washington, D.C. (1975). Neutralizing antibody was determined in chick embryo fibroblast cultures. Neutralization tests were for 200 $TCID_{50}$ of virus and used cytopathology and hemagglutination for detection of virus replication. Results are shown in Table 3, below.

TABLE 3

Antibody Response in p188-DNA-Immunized Compared with Amantadine-Rescued Birds

| DNA | No.[a] | Bleed | Antibody to Ck/Vic/85 (H7N7) HI | Neutralizing | ELISA (×10$^{-3}$) | Antibody to Ck/Penn/1370/83 (H5N2) ELISA (×10$^{-3}$) |
|---|---|---|---|---|---|---|
| p188 | 6 | 1 wk PB[b] | 5 (0–10) | 2 (0–10) | 2 (0–10) | < |
| | 6 | 2 wk PB | 8 (0–20) | 13 (0–33) | 5 (0–10) | < |
| | 5 | 1 wk PC[c] | 112 (80–160) | 873 (33–3333) | 640 (100–1000) | 26 (0–100) |
| | 5 | 2 wk PC | 272 (80–640) | 540 (33–1000) | 640 (100–1000) | 46 |
| None/ Aman. | 5 | 1 wk PB | <[d] | | < | < |
| | 5 | 2 wk PB | < | < | < | < |
| | 4 | 1 wk PC | < | < | < | |
| | 4 | 2 wk PC | 300 (80–640) | 442 (100–1000) | 1000 (1000) | 1000 (1000) |

Antibody titers are given as the median (range).
[a](No.) Number of chicks in group at time of bleed.
[b](wk PB) means weeks post boost.
[c](wk PC) means weeks post challenge.
[d](<) means all birds had titers of less than 10.

Analysis of the antibody responses in vaccinated and amantadine-rescued birds revealed that the p188-inoculations had primed an antibody response to H7. As in experiment 1 (Table 1), DNA vaccination and boost induced only low titers of antibody to H7. However, within one week of challenge, the DNA-immunized group had high titers of HI and neutralizing activity for H7. These titers underwent little (if any) increase over the next week. Furthermore, most of the post-challenge antibody in the vaccinated birds was directed against H7. This specificity was shown by comparing ELISA antibody titers to H7 virus (the immunizing hemagglutinin type) and H5 virus (a hemagglutinin type to which the birds had not been exposed). The post-challenge sera contained 20-times higher titers of ELISA antibody for the H7 than the H5 virus. By contrast, in the amantadine-rescued group, most of the antibody was not H7-specific and was directed against proteins that are common to the H5 and H7 virus. This was demonstrated by comparable titers of ELISA antibody for the H5 and the H7 influenza viruses.

EXAMPLE 3

Immunization of Chickens Using a Nonretroviral Transcription Unit

Figure 4A:
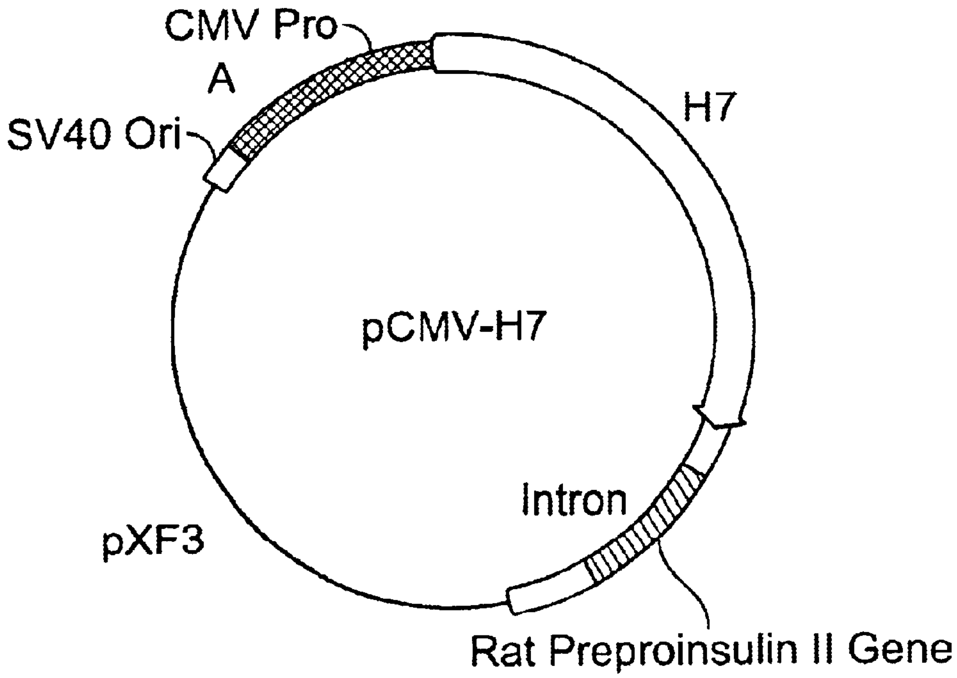
FIG. 4A is a schematic representation of the nonretroviral vector comprising the influenza virus antigen DNA transcription unit encoding subtype H7 hemagglutinin.
Figure 4B:
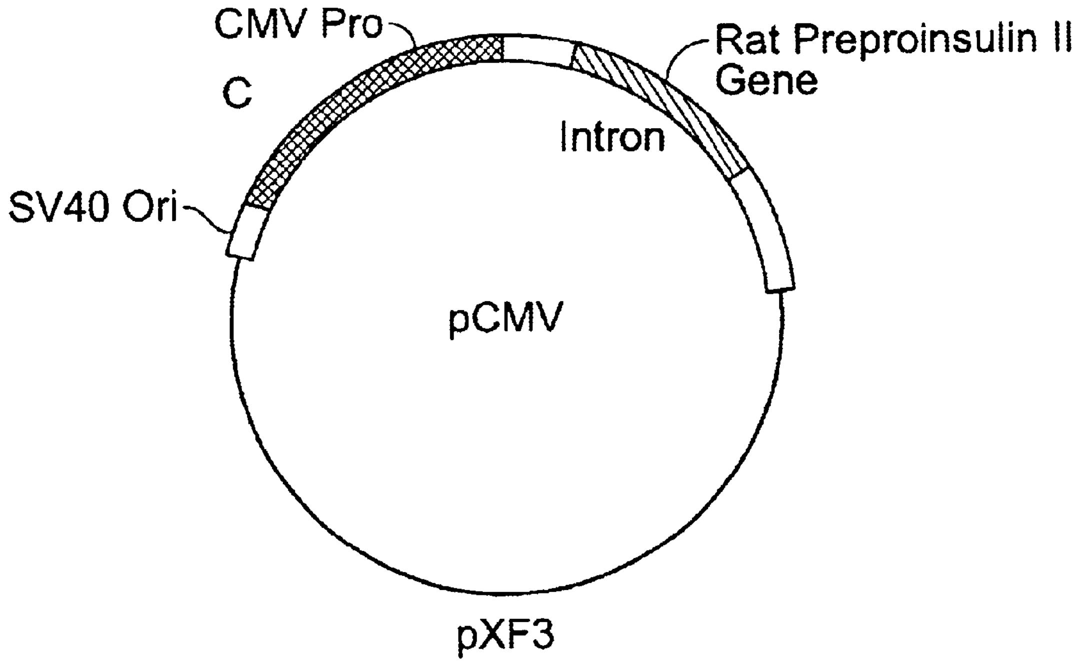
FIG. 4B is a schematic representation of the nonretroviral vector comprising a control DNA transcription unit, encoding no influenza virus antigens.

This experiment was performed in order to demonstrate that DNA transcription units devoid of retroviral DNA could be successfully employed to generate a protective immune response according to the methods herein described. The vectors used in this experiment to vaccinate chickens are shown in FIGS. 4A and 4B. FIG. 4A is a schematic representation of pCMV/H7, a plasmid capable of expressing the influenza virus H7 subtype hemagglutinin under the transcription control of a cytomegalovirus (CMV) immediate early promoter. FIG. 4B shows pCMV/control, a control plasmid which is not capable of expressing influenza antigens. These plasmids are derivatives of the pBC12/CMV vector of Dr. Bryan Cullen, Duke University, Durham, N.C. (Cullen, B. R., *Cell* 45:973–982 (1986)).

In the experiments using pCMV/H7 (the nonretroviral-based DNA transcription unit) to generate immune responses, immunization and boosts used the same inoculation schedule but different inoculation routes than described in Example 1. Specifically, 100 $\mu$g of DNA was inoculated by each of three routes: intravenous, intraperitoneal, and intramuscular. The boosts used the same DNA dose and sites of inoculation as the vaccinations. Challenge was 1–2 weeks after the boost, with 100 lethal doses$_{50}$ of Ck/Vic/85 used so as to achieve essentially 100% killing. Results of five independent trials of pCMV/H7 DNA are shown in Table 4, below.

TABLE 4

Protection Against a Lethal Ck/Vic/85 (H7N7) Influenza Virus Challenge by Immunization with pCMV/H7 DNA

| | Fate of challenge Group (# survivors/# tested) | |
|---|---|---|
| Trial | pCMV/H7 DNA | pCMV/Control DNA |
| 1 | 5/6 | 0/6 |
| 2 | 4/6 | 0/6 |
| 3 | 2/6 | 0/7 |
| 4 | 4/6 | 1/7 |
| 5 | 4/6 | 0/7 |
| Total | 19/30 | 1/33 |

In the five chicken trials using pCMV/H7 for vaccination, approximately 60% of the chickens were protected. This level of survival was very similar to that achieved with the retroviral-based vector p188 (Table 2). As in the trials with the retrovirus-based vector, many of the survivors developed transient signs of influenza. Thus, protection comparable to that achieved with the retrovirus-based vector could be achieved with a non-retroviral based vector.

Antibody responses to H7 in experiments with the non-retroviral-based vector were also similar to those with the retroviral-based vector (Table 3, Table 4). Specifically, protective responses were associated with the rapid rise (within one week) of H7-specific antibodies after challenge. Sera contained low to undetectable levels of anti-H7 antibodies after vaccination and boost. The low levels of antibody prechallenge coupled with the rapid rise in antibody post challenge suggest that protection was mediated by the DNA transcriptional units having established memory responses that were mobilized by the challenge infection. Thus, considerable protection has been achieved using nonretroviral DNA expression vectors (containing DNA transcription units encoding viral antigens) to vaccinate animals.

EXAMPLE 4

Figure 4C:
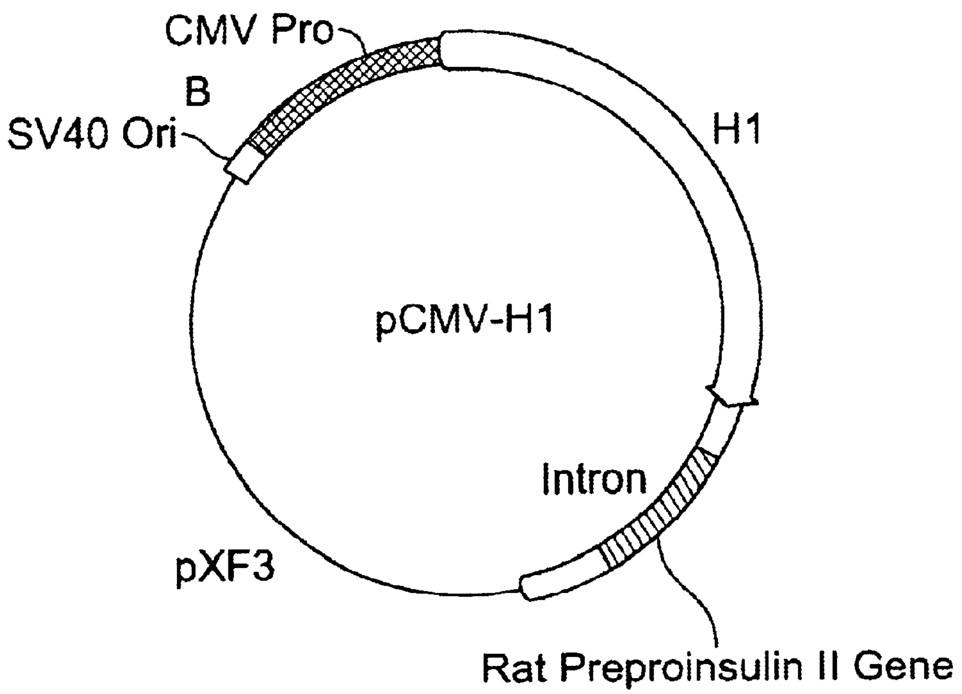
FIG. 4C is a schematic representation of the nonretroviral vector comprising the influenza virus antigen DNA transcription unit encoding subtype H1 hemagglutinin.

Immunization of Mice by Vaccination with pCMV/H1 DNA: Analysis of Various Routes of Inoculation A DNA transcription unit referred to as pCMV/H1 was successfully used to immunize mice against a lethal challenge with mouse adapted A/PR/8/34 H1N1 influenza virus. This transcription unit encodes an influenza type H1 hemagglutinin under the transcriptional regulation of the CMV immediate early promoter. The H1 influenza virus hemagglutinin gene used in this construct is described in more detail in Winters et al., *Nature* 292:72 (1981) and is identical to that in the challenge virus. The vector is the same as that used in Example 3 for the expression of H7 (See FIG. 4B). The pCMV/H1 transcription unit is depicted in FIG. 4C.

TABLE 5

Antibody Responses to the H7 Challenge Virus in pCMV/H7 and pCMV-control DNA inoculated chickens

| | | Control DNA-inoculated | | | CMV/H7 DNA/inoculated | | |
|---|---|---|---|---|---|---|---|
| Time of Bleed | Trial | HI | Neutralizing | ELISA ($\times 10^{-3}$) | HI | Neutralizing | ELISA ($\times 10^{-3}$) |
| 4 weeks post-vaccination (pre-boost) | 2 | < | < | < | < | < | < |
| | 3 | < | < | < | < | < | < |
| | 4 | < | < | < | < | < | < |
| | 5 | < | < | < | 2.5 | < | < |
| 1 week post-boost (pre-challenge) | 2 | < | < | < | < | < | < |
| | 3 | < | < | < | < | < | < |
| | 4 | < | < | < | 2.5 | < | 2.5 |
| | 5 | < | < | < | 2.5 | < | 2.5 |
| 2 week post-challenge | 2 | dead | dead | dead | 60 | 33 | 765 |
| | 3 | dead | dead | dead | 60 | 33 | 1000 |
| | 4 | dead* | dead* | dead* | 100 | 33 | 775 |
| | 5 | dead | dead | dead | 140 | 108 | 1000 |

*One control bird survived in this group. Its post challenge titers were HI, 80; Neutralizing, 10, and ELISA, 100.

Vaccine trials in mice were accomplished by the administration of DNA to 6- to 8-week-old BALB/c mice. Two DNA inoculations were given, one at time 0 and the second four weeks later. Test animals were observed throughout the trials and mice were weighed regularly beginning at the time of challenge. Lethal challenge was administered at 10 days after the second inoculation by inhalation of virus into the lungs of Metofane (Pitman-Moore, Mundelein, IL)-anesthetized mice. The challenge consisted of 250 plaque-forming units (10–100 times the median lethal dose ($LD_{50}$)) of mouse-adapted A/PR/8/34 (H1N1) influenza virus in 100 $\mu$l of saline supplemented with 0.1% bovine serum albumin. The challenge virus underwent localized replication in the respiratory/tract causing death due to pneumonia within 1–2 weeks. Routes of DNA inoculation included the following: intravenous (tail vein); intraperitoneal; intramuscular (both quadriceps); intranasal (DNA drops administered to the nares of mice anesthetized with Metofane); intradermal (foot pad); and subcutaneous (scruff of the neck). In general, 100 $\mu$g of DNA was administered in 100 $\mu$l of saline per test site. For foot-pad inoculations, 50 $\mu$g of DNA was administered in 25 $\mu$l.

Table 6 sets forth the results showing protection of the mice against a lethal A/PR/8/34 (H1N1) influenza virus challenge by inoculation of pCMV/H1 DNA in saline. Data in Table 6 are pooled from four independent trials. Routes shown are intravenous (iv), intraperitoneal (ip), intramuscular (im), intranasal (in), intradermal (id), and subcutaneous (sc). Signs of influenza included weight loss, ruffled fur, and lethargy. The signs were scored as follows: +, transient weight loss but maintenance of smooth fur and normal levels of activity; ++, transient weight loss, some ruffling of fur and lethargy; +++, transient weight loss and more severe ruffling of fur and lethargy; ++++, more pronounced weight loss coupled with severe ruffling of fur and lethargy; +++++, weight loss and severe signs of influenza leading to death. Probability was calculated by using Fisher's exact two-tailed test comparing the frequency of survival and mortality in vaccine versus control groups.

TABLE 6

Protection against Lethal A/PR/8/34 (H1N1) Challenge by Various Routes of pCMV/H1 Inoculation

| DNA | Route | Dose (μg) | Signs of Infl. | # Surv./ # Test | % Surv | Probability |
|---|---|---|---|---|---|---|
| pCMV/H1 | iv, ip, im | 300 | ++ | 21/22 | 95 | <0.0001 |
| | im | 200 | ++ | 18/19 | 95 | <0.0001 |
| | iv | 100 | ++ | 10/12 | 83 | <0.0001 |
| | in | 100 | +++ | 13/17 | 76 | <0.0001 |
| | id | 50 | ++++ | 9/12 | 75 | <0.001 |
| | sc | 100 | ++++ | 4/6 | 67 | <0.02 |
| | ip | 100 | +++++ | 0/6 | 0 | |
| pCMV/ control | various | 0–300 | +++++ | 3/24 | 13 | |

Excellent survival occurred in groups receiving intramuscular inoculations, intravenous inoculations, or inoculations by each of three routes (intramuscular, intravenous, and intraperitoneal). The relatively mild influenza that developed in these groups was associated with ruffling of fur and transient weight loss. Good survival, but more severe influenza, occurred in mice receiving DNA intranasally. Yet poorer survival (67–75%) and more severe signs of influenza occurred in mice receiving intradermal and subcutaneous inoculations. None of the mice receiving only intraperitoneal injections survived the lethal challenge. Control groups (inoculated with pCMV/control DNA or no DNA) developed severe signs of influenza with very few mice (13%) surviving the challenge. Thus, intramuscular, intravenous, intranasal and intradermal routes of administration each provided good protection.

These results indicate that the efficiency of transfection does not necessarily determine the efficiency of vaccination. The high ability of rodent muscle to take up and express DNA (Wolff, J. A. et al., *Science* 247:1465–1468 (1990); Wolff, J. A. et al., *BioTechniques* 11: 474–485 (1991); and Acsadi, G. et al., *New Biol.* 3:71–81 (1991)) did not correlate with an unusual efficiency of intramuscular vaccinations. Intramuscular inoculations worked well, but no better than, intravenous inoculations, and only somewhat better than the administration of DNA nose drops. Similar results were, obtained in chicken trials for route of inoculation (described below), where intravenous and intratracheal inoculations achieved levels of protection comparable with those provided by intramuscular inoculations.

EXAMPLE 5

Protective Immunizations by Different Routes of pCMV/H7 Inoculation in the Chicken Influenza Model The effect of the route of inoculation on DNA vaccination was further evaluated in the avian influenza virus model. The DNA vaccine trials for route of inoculation in chickens were conducted as described in Example 1. Routes of inoculation included the following: intravenous (wing vein): intramuscular (breast muscle): intratracheal (DNA drops administered to the trachea): subcutaneous (nape); intrabursal (injections just above the chicken's vent); and intraorbital (DNA drops administered to the eye). In general, 100 or 200 μg of DNA was administered in 200 μl of saline. Results are shown in Table 7, below. Data for p188 and pRCAS DNA are pooled from three independent trials. Data for pCMV/H7 and pCMV/control DNA are pooled from two independent trials. Probability was calculated by using Fisher's exact two-tailed test comparing the frequency of survival and mortality in vaccine versus control groups. Routes shown are intravenous (iv), intraperitoneal (ip), subcutaneous (sc), intramuscular (im), intratracheal (it), intrabursal (ib), and intraorbital (io).

TABLE 7

Protection of Chickens against a Lethal Ck/Vic/85 (H7N7) Challenge Following Different Routes of DNA Inoculation[a]

| DNA | Route | Dose (μg) | # Surv./ # test | % Surv. | Probability |
|---|---|---|---|---|---|
| | iv | 100 | 8/33 | 24 | <0.01 |
| | ip | 100 | 0/8 | 0 | |
| | sc | 100 | 0/2 | 0 | |
| pRCAS | iv, ip, sc | 300 | 1/55 | 2 | |
| | im | 200 | 3/10 | 30 | <0.02 |
| | it | 200 | 3/10 | 30 | <0.02 |
| | ib | 200 | 1/10 | 10 | |
| | io | 200 | 1/10 | 10 | |
| pCMV/ control | Various | 0–300 | 1/43 | 2 | |

[a]Data for controls is the same as in Tables 2 and 4.

In the chicken trials for route of inoculation, good efficacy was demonstrated for intravenous, intramuscular, and mucosal administration of the vaccine DNAs. These groups exhibited about one half the level of protection (24–30%) achieved in groups receiving DNA by each of three routes (Tables 2 and 4). Poor to no protection was achieved by subcutaneous, intraperitoneal, intrabursal, and intraorbital inoculations. Chickens receiving control DNA developed lethal influenza, with very few chickens (approximately 2%) surviving the challenge. Within experimental groups, surviving chickens showed variability in the severity of influenza-related illness.

EXAMPLE 6

Protective Immunizations by Gene Gun Delivery of DNA to the Mouse Epidermis

To test whether a DNA gun could be used to deliver DNA to the epidermis, the Accell particle bombardment device (Agracetus, Middleton, Wis.) was employed to deliver DNA-coated gold beads to the epidermis of mice. These experiments were done in collaboration with Dr. Joel R. Haynes of Agracetus, Inc.

For gene-gun delivery of DNA to mice, plasmid DNA was affixed to gold particles by adding 10 mg of 0.95 $\mu$m gold powder (Degussa, South Plainfield, N.J.) and an appropriate amount of plasmid DNA to a 1.5-ml centrifuge tube containing 50 $\mu$l of 0.1 M spermidine. Plasmid DNA and gold were coprecipitated by the addition of 50 $\mu$l of 2.5 M $CaCl_2$ during vortex mixing, after which the precipitate was allowed to settle and was washed with absolute ethanol and resuspended in 2.0 ml of ethanol. The gold/DNA suspension was transferred to a capped vial and immersed in a sonicating water bath for 2–5 seconds to resolve clumps. The 163 $\mu$l of the gold/DNA suspension was layered onto 1.8 cm×1.8 cm Mylar sheets and allowed to settle for several minutes, after which the meniscus was broken and excess ethanol was removed by aspiration. Gold/DNA-coated mylar sheets were dried and stored under vacuum. The total amount of DNA per sheet was a function of the DNA/gold ratio and ranged from 0.2 to 0.0002 $\mu$g per sheet. Animals were anesthetized with 30 $\mu$l of Ketaset/Rompun (10:2). Abdominal target areas were shaved and treated with Nair (Carter-Wallace, New York) for two minutes to remove residual stubble and stratum corneum. Target areas were thoroughly rinsed with water prior to gene delivery. DNA-coated gold particles were delivered into abdominal skin with the Accell instrument, which employs an electric spark discharge as the motive force (Yang, M. S. et al., *Proc. Natl. Acad. Sci. USA* 87: 9568–9572 (1990)). Each animal received two nonoverlapping deliveries per immunization, at a discharge voltage of 17 kV. The beads deliver DNA into cells, where the DNA dissolves and can be expressed (Yang, M. S. et al., *Proc. Natl. Acad. Sci. USA* 87: 9568–9572 (1990); Williams, R. S. et al., *Proc. Natl. Acad. Sci. USA* 88: 2726–2730 (1991)). Expression is transient, with most of the expression being lost within 2–3 days due to the normal sloughing of the epidermis (Williams, R. S. et al., *Proc. Natl. Acad. Sci. USA* 88: 2726–2730 (1991); unpublished observations).

Gene gun-based acceleration of DNA-coated gold beads into the epidermis proved to be by far the most efficient method of DNA immunization, as shown in Table 8. Data are pooled from four independent trials. Probability was calculated by using Fisher's exact two-tailed test comparing the frequency of survival and mortality in vaccine versus control groups. For the description of the signs of influenza, see above discussion of Table 6.

TABLE 8

Protection against Lethal A/PR/8/34 (H1N1) Challenge by Gene Gun-Delivered pCMV/H1 DNA Inoculation

| DNA | Dose ($\mu$g) | Signs of Infl. | # Surv./ # Test. | Surv. | Probability |
|---|---|---|---|---|---|
| pCMV/H1 | 0.4 | + | 21/22 | 95 | <0.0001 |
| | 0.04 | +++ | 7/11 | 64 | <0.001 |
| | 0.004 | +++++ | 0/5 | 0 | |
| | 0.0004 | +++++ | 0/4 | 0 | |

TABLE 8-continued

Protection against Lethal A/PR/8/34 (H1N1) Challenge by Gene Gun-Delivered pCMV/H1 DNA Inoculation

| DNA | Dose ($\mu$g) | Signs of Infl. | # Surv./ # Test. | Surv. | Probability |
|---|---|---|---|---|---|
| pCMV/ control | 0.4 | +++++ | 3/22 | 14 | |

These tests of gun-delivered DNA in the murine model demonstrated that as little as 0.4 $\mu$g of DNA was sufficient to achieve 95% survival. These survivors developed very limited to no signs of postchallenge influenza. Mice receiving 0.04 $\mu$g of gun-delivered pCMV/H1 DNA had an approximately 65% survival rate and suffered fairly severe signs of influenza. Mice that received 0.004 $\mu$g or 0.0004 $\mu$g of pCMV/H1 DNA succumbed to the challenged. As in tests of saline injections, mice receiving control DNA developed severe signs of influenza and had very limited survival (14%). Thus, highly efficient immunizations were achieved by gene-gun delivery of DNA to the epidermis of mice. This method of immunization required 250–2500 times less DNA than the saline inoculations (0.4–0.004 $\mu$g as opposed to 100–200 $\mu$g of DNA) (See Tables 6 and 7).

EXAMPLE 7

Antibody Responses in pCMV/H1 Vaccinated Mice

In the murine trials described above in Examples 4 and 6, sera were collected immediately prior to each DNA inoculation, immediately prior to challenge, and at two times after challenge. Anesthetized mice were bled from the eye vein into 40 $\mu$l nonheparinized microhematocrit tubes. Sera for members within a group were pooled. Hemagglutination inhibition assays were performed with chicken red blood cells and mouse serum that had been pretreated with kaolin to remove background activity (Novak, M. et al., *Vaccine* 11: 55–60 (1993)). Hemagglutination inhibition titers are the reciprocal of the highest serum dilution giving complete inhibition of hemagglutination. The isotypes of mouse antibodies were determined by enzyme-linked immunosorbent assay (ELISA) using standard protocols and microwell plates coated with purified A/PR/8/34 (H1N1) influenza virus. These assays used 1:1000 dilutions of isotype-specific peroxidase-conjugated antibodies that had been provided at titers with similar activities (Sigma Immuno-Chemicals). Data for serum analysis are shown below in Table 9. Data are the geometric means of the reciprocal of the final dilutions of pooled sera that scored positive for a given condition.

TABLE 9

Antibody Responses in Vaccine Trials Testing Routes of pCMV/H1 DNA Inoculation in Mice

| | | | Titers of Antibody to A/PR/8/34 (H1N1) | | | |
|---|---|---|---|---|---|---|
| | | | | ELISA value ×$10^{-2}$ | | |
| Route | Bleed | # Test. | HI | IgM | IgG | IgA |
| | | pCMV/H1 in saline | | | | |
| iv | Prevac | 2 (12) | < | < | < | < |
| | 10 d PB | 2 (12) | < | < | 8 | 4 |
| | 4 d PC | 1 (6) | 20 | < | 8 | 4 |
| | 14–19 d PC | 2 (10) | 113 | 1 | 256 | 4 |
| im | Prevac | 3 (19) | < | < | < | < |
| | 10 d PB | 3 (19) | < | < | 3 | < |
| | 4 d PC | 2 (13) | 6 | < | 32 | 2 |
| | 14–19 d PC | 3 (18) | 127 | < | 406 | 2 |
| in | Prevac | 3 (17) | < | < | < | < |
| | 10 d PB | 3 (17) | < | < | 2 | 1 |
| | 4 d PC | 2 (11) | < | 1 | 2 | 1 |
| | 14–19 d PC | 3 (17) | 160 | 2 | 202 | 2 |
| | | pCMV/control in saline | | | | |
| various | Prevac | 3 (16) | < | < | < | < |
| | 10 d PB | 3 (16) | < | < | < | < |
| | 4 d PC | 2 (9) | < | < | < | < |
| | 14–19 d PC | 1 (2) | 320 | < | 256 | < |
| | | pCMV/H1 | | | | |
| gene | Prevac | 2 (10) | < | < | < | < |
| gun | 10 d PB | 3 (16) | 10* | 1 | 10 | < |
| | 4 d PC | 3 (16) | 20* | 2 | 64 | < |
| | 14–19 d PC | 3 (15) | 160* | 2 | 64 | < |
| | | pCMV/control | | | | |
| gene | Prevac | 2 (12) | < | < | < | < |
| gun | 10 d PB | 3 (16) | < | 1 | < | < |
| | 4 d PC | 3 (16) | < | 2 | < | < |
| | 14–19 d PC | 1 (3) | NT | 4 | 512 | < |

*Only one of the three pools of sera was tested for HI activity. Prevac = bleed before DNA vaccinations: 10 d PB; bleed 10 days after the second DNA inoculation (prior to challenge); 4 d PC, bleed 4 days post challenge. # Test. = the number of groups for which pooled sera were assayed (total number of animals contributing sera to the pools). NT = not tested. < = activity not detected in the lowest dilution of serum used in tests.

DNA vaccinations by the various routes appeared to prime memory antibody responses. The DNA vaccinations and booster inoculations raised only low to undetectable titers of hemagglutination-inhibiting antibodies and ELISA activity. These low levels of activity underwent rapid increases after challenge. As in the chicken experiment (Tables 3 and 5) protection occurred in animals that did not have detectable levels of anti-influenza antibodies before challenge. However, the best protection occurred in groups in which the DNA inoculations had raised detectable titers of prechallenge antibody.

Use of ELISAs to score the isotypes of the anti-influenza virus antibodies demonstrated that the immunizations had primed IgG responses. Low titers of anti-influenza IgG could be detected prechallenge in the sera of mice vaccinated by gun delivery, intravenous or intramuscular inoculations of DNA. Borderline to undetectable titers of IgG were present in the sera of mice receiving DNA nose drops (consistent with the poorer protection provided by this route of DNA administration). By four days after challenge, increased levels of IgG were detected in mice undergoing the best protection. By contrast, mice receiving control DNA did not have detectable levels of anti-influenza virus IgG until the second serum collection after challenge. This was consistent with vaccinated, but not control, groups undergoing a secondary antibody response to the challenge.

These experiments show that the DNA inoculation had primed both T-helper and B-cell memory. This memory appeared to provide protection by supporting the mounting of secondary responses in challenged animals. Evidence for the priming of memory is provided by the DNA inoculations raising antibodies belonging to the IgG isotype, as IgG is produced by differentiated plasma cells that have undergone immunoglobulin rearrangements in response to T-cell help (Abbas, A. K. et al., Cellular and Molecular Immunology (Saunders, Philadelphia, Pa.), pp. 187–197 (1991)). Evidence for the mobilization of memory in response to the challenge is found in the rapid increases in serum IgG after challenge.

Marginal to undetectable levels of IgM and IgA were detected in both prechallenge and postchallenge sera. The low levels of these immunoglobulin isotypes throughout the trials indicated that none of the routes of DNA inoculation were effective at raising serum IgM or IgA.

EXAMPLE 8

Use of pCMV/H1 DNA Transcriptional Unit to Protect Ferrets Against A/PR/8/34(H1N1) Influenza Challenge Studies on pCMV/H1 DNA immunization in a ferret model were undertaken because this influenza model has many similarities to human influenza infections. In the initial experiment, ferrets were immunized with purified pCMV/H1 DNA in saline by intramuscular inoculations at a one month interval. Young adult female ferrets were prebled and vaccinated with 500 μg of pCMV/H1 or pCMV/control DNA in saline by two injections of 125 μl in each hind leg for a total inoculation volume of 500 μl. One ferret received three intramuscular inoculations of 500 μg of pCMV/H1 DNA at one month intervals while a second animal received two intramuscular inoculations of 500 μg of DNA at one month intervals. The control animal received three 500 μg intramuscular inoculations of pCMV/control DNA at one month intervals.

Metofane-anesthetized ferrets were challenged with $10^{7.7}$ egg infectious doses$_{50}$ of A/PR/8/34 (H1N1) via the nares at one week after the final DNA inoculation. Nasal washes were collected at days 3, 5 and 7 post challenge under ketamine anesthetic. Titration of virus in nasal washes was done in eggs as described (Katz, J. M. and R. G. Webster, *J. Infect. Dis.* 160: 191–198 (1989)). Data are presented in Table 10, below.

TABLE 10

Protection of Ferrets against an H1 Virus by Intramuscular Inoculation of pCMV/H1 DNA

| DNA | No. of DNA Adminis-trations | Ferret ID No. | Virus Titer in Nasal Washes, $\log_{10}$ egg infectious $doses_{50}$/ml day 3 | day 5 | day 7 |
|---|---|---|---|---|---|
| pCMV/H1 | 3 | 901 | 5.5 | 1.5 | <1 |
| | 2 | 903 | 5.7 | 4.7 | <1 |
| pCMV/control | 3 | 907 | 6.5 | 6.2 | <1 |

Analyses of nasal washes revealed similar high titers of virus in the washes of all of the ferrets at 3 days post challenge. Interestingly, the ferret receiving three inoculations of pCMV/H1 had largely cleared the nasal infection by five days post challenge, with its five day nasal wash containing less than 10 egg infectious $doses_{50}$ of virus per ml. At this time the ferret receiving two inoculations of pCMV/H1 DNA had a ten fold reduction in the titer of virus in its nasal wash. By contrast, the ferret receiving control DNA had modest if any reduction in the titer of virus in its nasal wash. By 7 days post challenge, all of the ferrets had cleared their nasal infections. The much more rapid clearing of virus in the ferret receiving three intramuscular inoculations of pCMV/H1 DNA and the somewhat more rapid clearing of virus in the ferret receiving two intramuscular inoculations of pCMV/H1 DNA than in the two ferrets receiving control DNA suggest that the intramuscular inoculations of pCMV/H1 had raised some anti-influenza immunity.

Gene Gun Inoculation

To increase the efficiency of the induction of immunity, a second experiment was undertaken in ferrets using the Accell gene gun to deliver DNA coated gold beads into the skin of ferrets. The abdominal epidermis was used as the target for gene gun delivered DNA with ferrets receiving two gene gun administrations of DNA at a one month interval. Gene gun inoculations were delivered to Ketamine-anesthetized young adult female ferrets. Skin was prepared by shaving and treating with the depilatory agent NAIR (Carter-Wallace, New York). DNA beads (1 to 3 microns) were prepared for inoculations as previously described (Fynan et al., *Proc. Natl. Acad. Sci. USA* 90:11478–11482 (1993)). A delivery voltage of 15 kV was used for inoculations. Ferrets were inoculated with either 2 μg or 0.4 μg of DNA. Ferrets inoculated with 2 μg of DNA received 10 shots with each shot consisting of 0.8 mg of beads coated with 0.2 μg of DNA. Ferrets receiving 0.4 μg of DNA received two of these shots.

Metofane-anesthetized ferrets were challenged at one week after the second DNA immunization by administration of $10^{6.7}$ egg infectious doses of A/PR/8/34 (H1N1) virus via the nares. This challenge was 10 fold lower than in the experiment using intramuscular inoculation because of the high levels of virus replication in the first challenge. Nasal washes were collected at days 3 and 5 post challenge under ketamine anesthetic and the virus titered as described above. Data are presented in Table 11, below.

TABLE 11

Protection of Ferrets against an H1 Virus by Gene Gun Inoculation of pCMV/H1 DNA

| DNA | Amount of DNA (μg) | Ferret ID No. | Virus Titer in Nasal Washes, $\log_{10}$ egg infectious $doses_{50}$/ml day 3 | day 5 |
|---|---|---|---|---|
| pCMV/H1 | 2 | 927 | <1 | <1 |
| | | 931 | <1 | <1 |
| | | 933 | <1 | <1 |
| | 0.4 | 926 | 4.3 | <1 |
| | | 929 | 3.9 | <1 |
| | | 933 | <1 | <1 |
| pCMV/control | 2 | 932 | 3.5 | <1 |
| | | 934 | 3.7 | <1 |

Analyses of post-challenge nasal washes in gene gun vaccinated ferrets revealed that the three ferrets receiving 2 μg of DNA and one of the three ferrets receiving 0.4 μg of DNA were completely protected from the challenge. This was shown by the inability to recover virus in the nasal washes of these animals at 3 days post challenge. The remaining two animals receiving 0.4 μg of DNA and the control animals were not protected, with easily detected titers of virus present in the nasal washes of the animal at three days post challenge. In this experiment, all animals (control and vaccinated) had no detectable virus in their nasal washes by five days post challenge.

Ferrets from the gene gun experiment were next analyzed for antibody responses to the DNA administrations and to the challenge virus. These assays tested for neutralizing activity for A/PR/8/34 (H1N1). The titrations of antibodies were done as described (Katz, J. M. and R. G. Webster, *J. Infect. Dis.* 160: 191–198 (1989)). Titers of neutralizing activity are the reciprocals of the highest dilution of sera giving complete neutralization of 200 50% tissue culture infectious doses of virus. Data are presented in Table 12, below.

TABLE 12

Neutralizing Antibody in Ferrets Vaccinated with Gene Gun-Delivered pCMV/H1 DNA and Challenged with A/Pr/8/34 (H1N1) Influenza Virus

| DNA | Amount of DNA (μg) | Ferret ID No. | Neutralizing Antibody: Pre-inoculation | Post-boost, pre-challenge | Post challenge (7 days) | Post challenge (14 days) |
|---|---|---|---|---|---|---|
| pCMV/H1 | 2 | 927 | <10 | <10 | 251 | 178 |
| | | 931 | <10 | 79 | 251 | 178 |
| | | 933 | <10 | 13 | 398 | 398 |

TABLE 12-continued

Neutralizing Antibody in Ferrets Vaccinated with Gene Gun-Delivered pCMV/H1 DNA and Challenged with A/Pr/8/34 (H1N1) Influenza Virus

| | | | Neutralizing Antibody | | | |
|---|---|---|---|---|---|---|
| DNA | Amount of DNA (μg) | Ferret ID No. | Pre-inoculation | Post-boost, pre-challenge | Post challenge (7 days) | Post challenge (14 days) |
| | 0.4 | 926 | <10 | <10 | 2511 | 2511 |
| | | 929 | <10 | <10 | 398 | 126 |
| | | 933 | <10 | <10 | 794 | 562 |
| pCMV/control | 2 | 932 | <10 | <10 | 562 | 398 |
| | | 934 | <10 | <10 | 562 | 794 |

Neutralizing antibody post DNA boost but prior to challenge was detected in two of the animals receiving 2 μg of gene gun-delivered DNA. No neutralizing antibody was detected in the pre-challenge sera of the third animal receiving 2 μg of DNA (an animal that was completely protected against the presence of virus in nasal washes). Neutralizing antibody was also not detected in the sera of the ferret receiving 0.4 μg of DNA that did not develop virus in its nasal wash.

In animals with prechallenge antibody, protection was presumably due to the presence of neutralizing antibody as well as the mobilization of memory responses for neutralizing antibody. In protected animals without detectable levels of prechallenge antibody, protection was likely due to the rapid mobilization of memory responses by the infection, with the mobilized responses controlling the infection. Protection in vaccinated animals in the absence of prechallenge antibody has also been observed in prior DNA vaccination studies in mice and chickens (see Tables 3, 5 and 9) (Fynan et al., *Proc. Natl. Acad. Sci. USA* 90:11478–11482 (1993); Robinson et al., *Vaccine* 11: 957–960 (1993)) and in vaccine trials using retrovirus and pox virus vectors to express the influenza virus hemagglutinin glycoprotein (Hunt et al., *J. Virol.* 62:3014–3019 (1988); Webster et al., *Vaccine* 9: 303–308 (1991)).

EXAMPLE 9

Microsphere-encapsulated DNA for Mucosal Administrations

The mucosal route of DNA inoculation was further developed by testing for the ability of microsphere-encapsulated DNA to raise protective responses against a lethal influenza virus challenge. The murine influenza virus model was used for these studies. pCMV/H1 and pCMV/control DNA were encapsulated in alginate microspheres at the Virus Research Institute, Inc., Cambridge, Mass. A trial was conducted in which each group received a primary inoculation and a boost. Group A received 0.4 μg of gene gun delivered DNA for the primary and no boost. Group B received 0.4 μg of gene gun delivered DNA for the primary and the boost. Group C received 0.4 μg of gene gun delivered DNA for the primary and 100 μg of alginate-encapsulated DNA for the boost. Group D received 100 μg of alginate-encapsulated DNA for both the primary and boost inoculations. Each administration of alginate-encapsulated DNA was delivered in 100 μl of water to the nares of Metofane-anesthetized mice. Lethal challenge with 500 pfu of A/PR/8/34 (H1N1) influenza virus was administered via the nares to metofane-anesthetized mice at 10 days after the second DNA inoculation. Four control groups received pCMV/control DNA at the same amounts and following the same regimen as the groups receiving pCMV/H1 DNA. Data for this experiment are presented in Table 13.

TABLE 13

Protection of Mice Against a Lethal Influenza Virus Challenge by Administration of Vaccine DNA in Microspheres

| | | pCMV/H1 DNA | | pCMV/Control DNA | |
|---|---|---|---|---|---|
| DNA | Boost | Signs of Infl. | Surv./ Total | Signs of Infl. | Surv./ Total |
| 0.4 μg, gun* | none | +++ | 3/6 | ++++ | 2/6 |
| 0.4 μg, gun | 0.4 μg, gun | — | 6/6 | +++++ | 1/6 |
| 0.4 μg, gun | 100 μg, ms i.n. | ++ | 5/6 | ++++ | 2/6 |
| 100 μg, ms i.n. | 100 μg, ms i.n. | + | 4/6 | ++++ | 1/4 |

*gun = gene gun delivery;
ms i.n. = DNA encapsulated in alginate microspheres

The intranasal administration of alginate-encapsulated DNA provided good protection. Each of the vaccine groups receiving alginate-encapsulated pCMV/H1 DNA exhibited much better survival than the groups receiving alginate-encapsulated pCMV/control DNA. Four out of 6 of the mice receiving only alginate-encapsulated DNA survived with very modest signs of influenza. By contrast, only one out of 4 mice receiving alginate-encapsulated control DNA survived. All of the control group developed severe signs of influenza. The group receiving only one gun inoculation exhibited moderate signs of influenza and had a 50% survival rate (3/6 mice). Addition of an alginate boost provided better protection against signs of influenza and a higher survival rate (5/6 mice surviving). Two gene gun deliveries of DNA provided the best survival, with all of the mice surviving with no signs of influenza.

EXAMPLE 10

Immunization of Mice Using a DNA Transcription Unit Encoding a Rotavirus Protein A rotavirus DNA transcription unit was tested for its ability to immunize mice. The pCMV/VP7 vector used in this experiment to vaccinate mice for rotavirus is similar to those shown in FIGS. 4A and 4C, except that the plasmid pCMV/VP7 is one capable of expressing the murine rotavirus neutralization capsid protein VP7. VP7 DNA was obtained from Dr. Harry Greenberg, Stanford University, Palo Alto, Calif., USA.

In the mouse experiments using pCMV/VP7 to generate immune responses, 0.4 μg of DNA was gene gun delivered to abdominal skin (as described above). All vaccinations were followed by a boost 4 weeks later. The boosts used the same DNA dose and sites of inoculation as the vaccinations. Testing for antibody and cytotoxic T cells (CTL) was 1–2 weeks after the boost. Data are shown in Table 14 and FIG. 5.

TABLE 14

Anti-VP7 Antibody in Sera of pCMV/VP7 DNA Inoculated Mice

| | $OD_{492nm}$ (X ± SD, n = 3)* | | | |
|---|---|---|---|---|
| | Preinoculation Sera | | Immune Sera | |
| Inoculation | 1:50 | 1:200 | 1:50 | 1:200 |
| pCMV/VP7-gun | 0.041 ± 0.040 | 0.000 ± 0.000 | 0.430 ± 0.220 | 0.130 ± 0.185 |
| pCMV-gun | 0.050 ± 0.070 | 0.050 ± 0.058 | 0.000 ± 0.000 | 0.044 ± 0.052 |
| EDIM-p.o. | 0.000 ± 0.000 | 0.000 ± 0.000 | 0.629 ± 0.220 | 0.589 ± 0.184 |

*Anti-VP7 antibody was tested by ELISA against whole mouse EDIM rotavirus.

The antibody ELISA titers against whole EDIM virus raised by pCMV/VP7 DNA are shown in Table 14. Antibody titers of 1:200 were raised by the DNA transcriptional unit for the VP7 gene (pCMV/VP7). The titer of antibody obtained by one inoculation of live EDIM murine rotavirus gave a titer of 1:800 (not shown). No significant titer was obtained by the pCMV/control plasmid alone.

Figure 5:
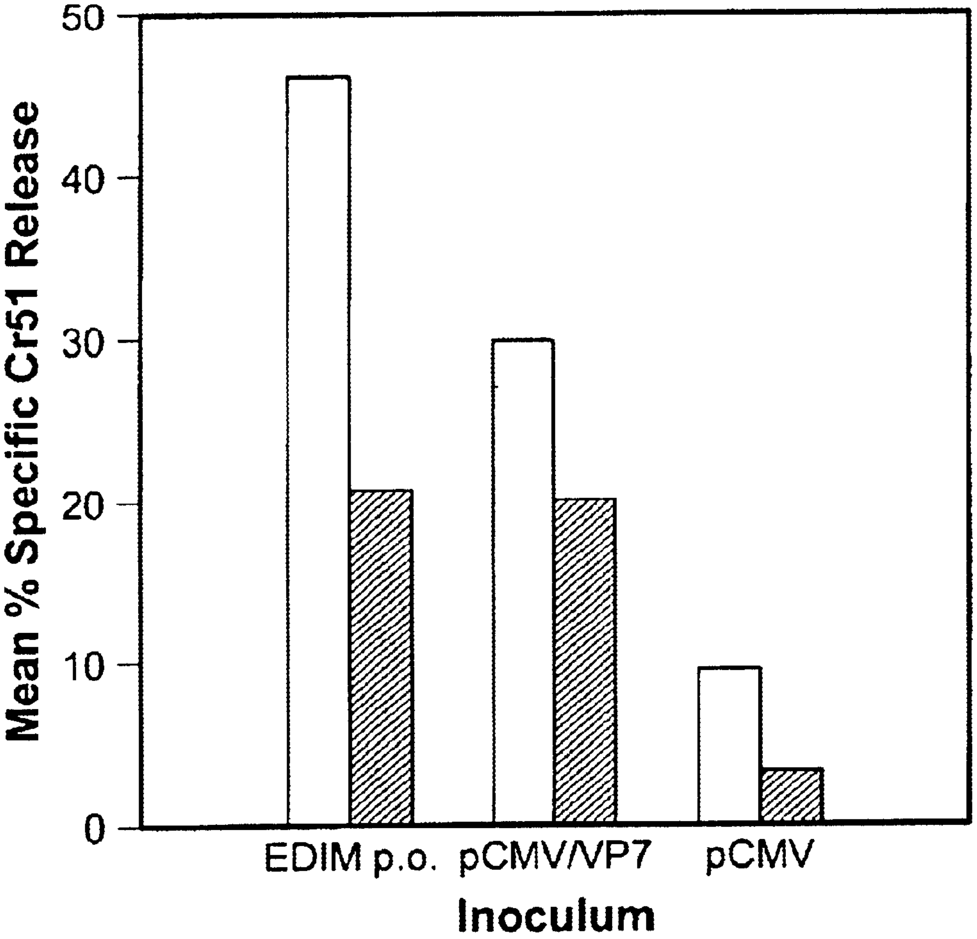
FIG. 5 is a bar graph depicting the cytotoxic T cell response of mice inoculated by gene gun with EDIM VP7 rotavirus cDNA in comparison with controls. Filled bars, effector to target ratio 60:1; striped bars, effector to target ratio 30:1.

It was also found that the plasmid pCMV/VP7 was able to induce a cytotoxic T cell (CTL) response against murine rotavirus infected cells. The results of a chromium-release CTL assay are shown in FIG. 5. The percent specific lysis in spleen cells from mice inoculated with pCMV/VP7 was approximately 30% at an effector to target ratio of 60:1, compared to 45% lysis obtained with mice orally infected with EDIM rotavirus.

EXAMPLE 11

DNA Constructs for Immunization Against HIV-1

Two series of DNA transcription units are prepared for immunizations against HIV-1. The first of these uses the pBC12/CMV vector (See above and FIG. 4B) to provide transcriptional control elements for HIV-1 sequences. In pBC12/CMV vectors, HIV-1 protein expression is Rev dependent. The second series uses the JW4303 vectors developed at James I. Mullins laboratory (Stanford University) (Palo Alto, Calif.) (see FIG. 6). These vectors support Rev-independent expression of Env. The JW4303 vectors and accompanying oligonucleotides are designed to facilitate the cloning of PCR amplified fragments of the Env of any isolate of HIV-1.

pBC12/CMV Based Vectors

Figure 7A:
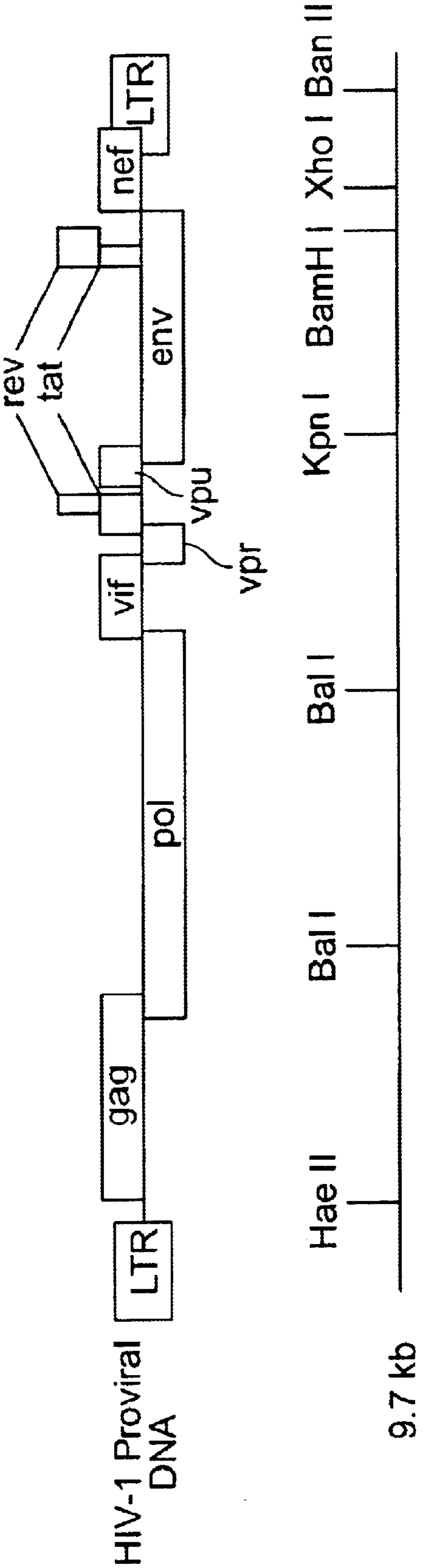
FIG. 7A is a schematic representation of HIV-1 proviral DNA.
Figure 7B:
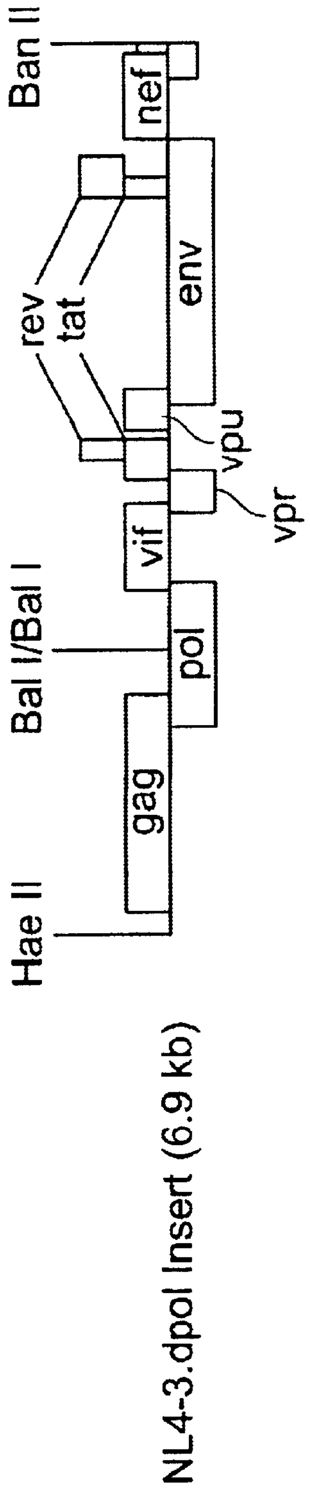
FIG. 7B is a schematic representation of the NL4-3.dpol insert.

All cloning into the pBC12/CMV based vectors was performed in pBC12/CMV/IL2. Specifically, insert fragments were substituted for the BamHI to HinDIII fragment of IL-2 CDNA. Three inserts have been used in these clonings (FIGS. 7B–7D).

pCMV/HIV-1-NL4-3.dpol (NL4-3.dpol) (FIG. 7B)

Figure 7C:
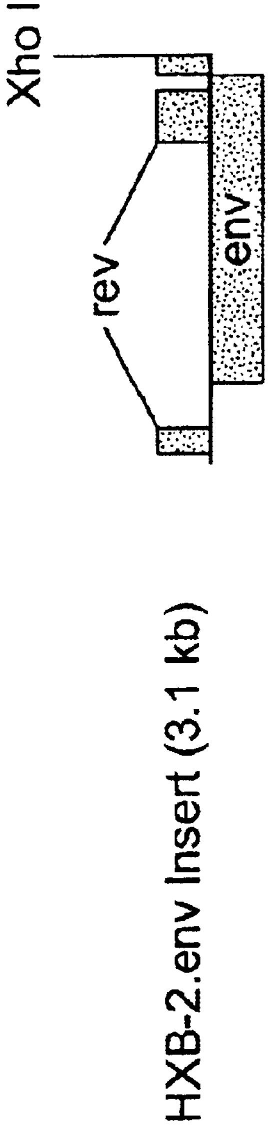
FIG. 7C is a schematic representation of the HXB-2.env insert.
Figure 7D:
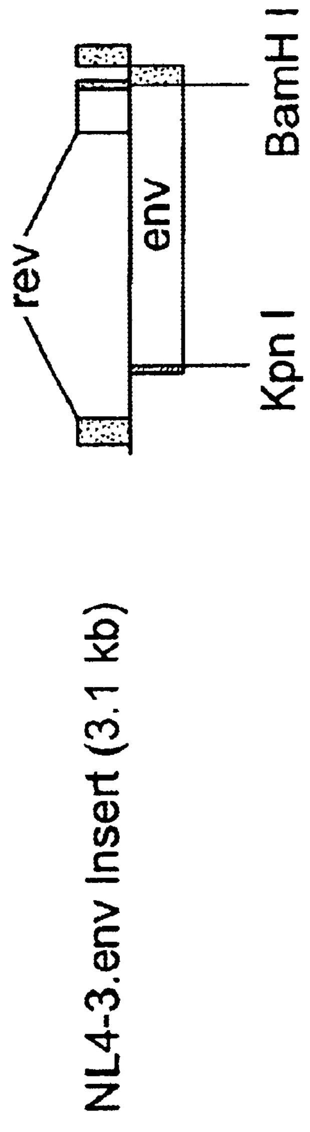
FIG. 7D is a schematic representation of the NL4-3.env insert.
Figures 8A, 8B, 8C, 8D:
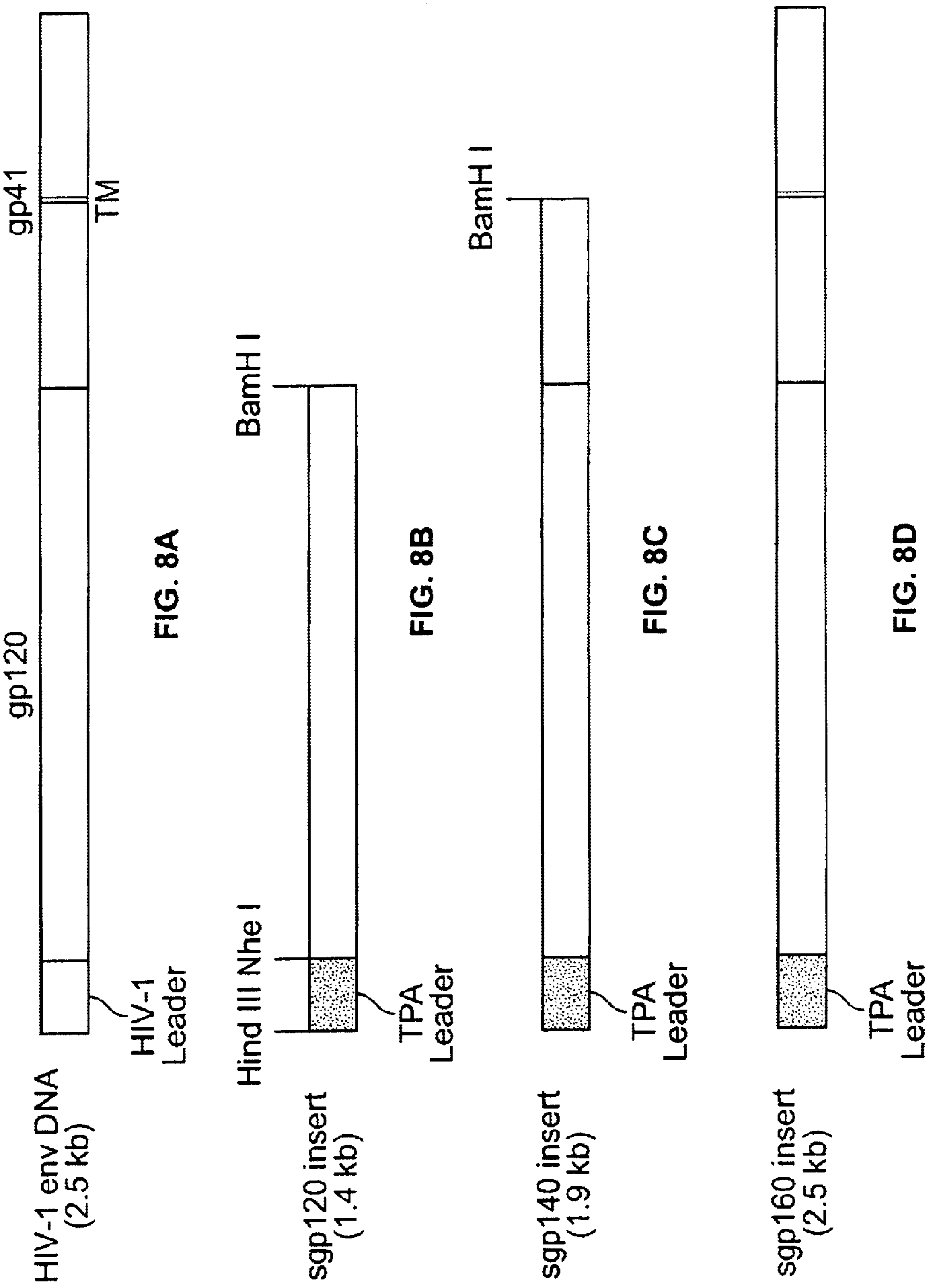
FIG. 8A is a schematic representation of HIV-1 env DNA.
FIG. 8B is a schematic representation of a sgp120.env insert.
FIG. 8C is a schematic representation of a sgp140.env insert.
FIG. 8D is a schematic representation of a sgp160.env insert.

FIG. 7A depicts HIV-1-NL4-3 (NL4-3) proviral DNA and its associated long terminal repeats (LTR) sequences and open reading frames. pNL4-3 was provided by Dr. Malcolm A. Martin's Laboratory (National Institutes of Health, Bethesda, Md.) (Adachi, et al., J. Virol. 59:284–291 (1986)). The Genbank accession number for strain HIV.NL4-3 is M1991. NL4-3.dpol inserts were constructed to encode non-infectious HIV-1 particles and to mimic a live but non-infectious infection. To achieve an insert that would encode non-infectious particles, the entire 5' and most of the 3' LTR were deleted from pNL4-3 using HaeII and BanII digestions respectively. The pol gene was rendered non-functional by a 1932 bp internal BalI deletion. Western blot analyses of transfected Cos cells were used to demonstrate the expression of Gag and Env. Gag and Env proteins were present both in cells and in culture medium. This was anticipated because Gag is the only HIV-1 protein required for particle formation.

pCMV/HIV-1-HXB-2.env (HXB-2.env) (FIG. 7C)

HXB-2.env was designed to express complete HXB-2 Env and Rev. The Genbank accession numbers for strain HIV.HXB2 are K03455 and M38432. Rev was included in the construct because expression of the normal HIV-1 Env is Rev dependent. This construct was achieved by substituting the SalI to XhoI fragment of the pSVIII.env construct of Dr. Joseph Sodroski (Dana Farber Cancer Institute, Boston, Mass.) (Helseth, et al., *J. Virol.* 64:2416–2420 (1990)) for the BamHI to HindIII fragment of IL-2 in pBC12/CMV/IL-2. Western blot analyses of transfected Cos cells demonstrated the expression of Env.

pCMV/HIV-NL4-3.env (NLV-3.env) (FIG. 7D)

A second example of a construct expressing HIV-1 Env and REV, NL4-3.env, expressed HXB-2/NL4-3 Env fusion proteins and Rev. In this construct, unique restriction sites near the ends of the HXB-2 env, KpnI and BamHI, were used to substitute NL4-3 sequences for homologous HXB-2 env sequences in pCMV/HXB-2.env. Western blot analyses of transfected Cos cells demonstrated the expression of Env.

JW4303 Based Vectors

Figure 6:
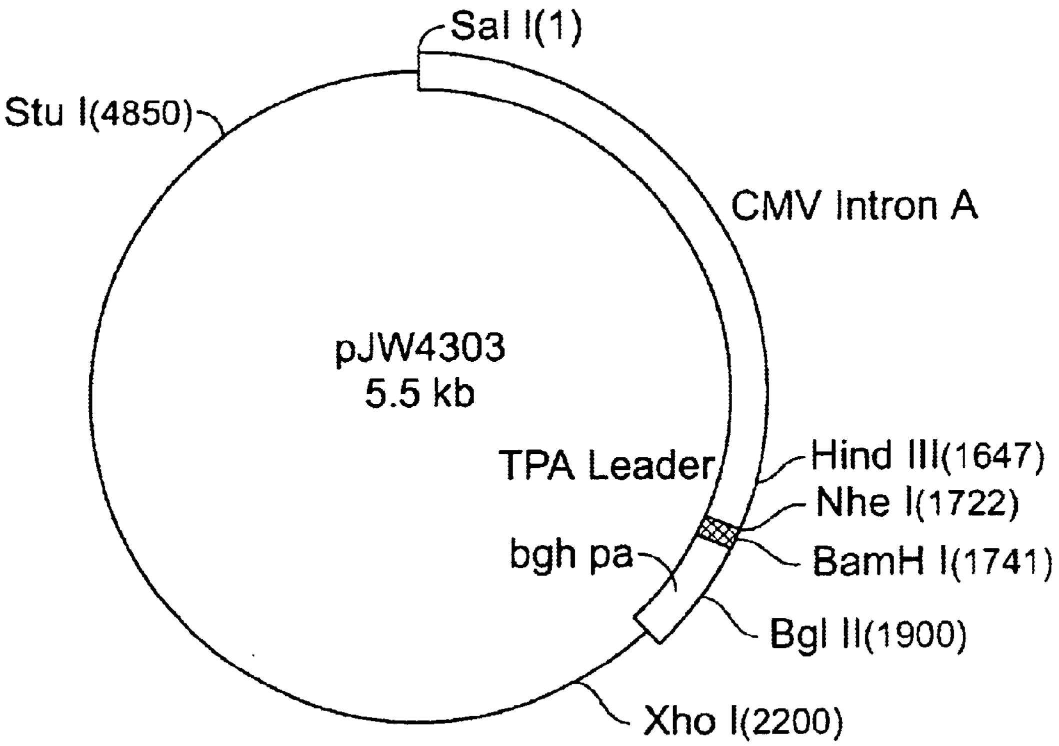
FIG. 6 is a schematic representation of the pJW4303 vector comprising the CMV intron A, a leader sequence for the tissue plasminogen activator (TPA) protein, and bovine growth hormone polyadenylation sequences.

The JW4303 plasmid uses ~2000 bp from the CMV immediate early promoter and sequences from the bovine growth hormone for insert expression (FIG. 6). Sequences from the CMV immediate early promoter include sequences encoding the CMV intron A. This intron can enhance the expression of inserted genes (Chapman, et al., *Nucleic Acids Research* 14:3979–3986 (1991)). The JW4303 vector includes a synthetic leader sequence for the tissue plasminogen activator (TPA) protein. This synthetic leader provides the start site for Env expression. The tissue plasminogen activator leader facilitates synthesis and secretion of glycosylated proteins (Haigwood, et al., *Prot. Eng.* 2:611–620 (1989)). PCR amplification from designer oligonucleotides is used to create env fragments that are inserted in-frame with the TPA leader. Consensus 5' oligonucleotides for sequences in different subgroups of HIV-1 allow the fusion of any HIV-1 env sequences to the TPA leader at or near the normal end of the mature Env. The oligonucleotides are designed to allow the use of unique restriction sites in the synthetic TPA leader for subcloning into JW4303. For example, the 5' oligonucleotide JApcr503 includes an XbaI site that allows fusion of the TPA leader just prior to amino acid 6 of the mature Env for subgroup B isolates of HIV-1.

Three types of antisense oligonucleotides allow construction of secreted gp120 (sgp120), secreted gp140(sgp140), or a normal gp160 form of Env (see FIGS. 8A–8D). DNA fragments encoding sgp120 forms of Env are synthesized using consensus antisense oligonucleotides at or near sequences encoding the proteolytic cleavage site between gp120 and gp41. An example of such an oligonucleotide for subgroup B virus is JApcr504 (SEQ ID NO. 2). DNA encoding sgp140 forms of Env are synthesized using an antisense oligonucleotides for consensus sequences at or near the membrane anchor domain of gp41. An example of such an oligonucleotide for subgroup B viruses is JApcr502 (SEQ ID NO. 3). DNAs encoding complete Envs are synthesized using oligonucleotide encoding consensus sequences within the cytoplasmic domain or 3' to the C-terminus of gp160. An example of such an oligonucleotide for subgroup B HIV-1 is JApcr506. The antisense oligonucleotides have unique restriction sites that facilitate cloning into JW4303 or derivatives of JW4303. For example JApcr502 and JApcr504 contain BamHI sites for cloning into the unique BamHI site in JW4303.

JW4303/HIV-1-HXB-2.sgp120 (HXB-2.sgp120)

HXB-2.sgp120 (See FIG. 8B) was synthesized using JApcr503 (gtcgctcctctagattgtgggtcacagtctattatggggtacc) (SEQ ID NO. 1) and JApcr504 (ggtcggatccttactgcaccactcttctctttgcc) (SEQ ID NO. 2) to amplify sequences from pCMV/HXB-2.env. The amplified fragments were digested with XbaI and BamHI and subcloned into NheI and BamHI digested JW4303. Western blot analyses of transfected Cos cells revealed sg120 in both the transfected cells and the culture medium.

JW4303/HIV-1-HXB-2.sgp 140 (HXB-2.sgp140)

HXB-2.sgp140 (See FIG. 8C) was constructed using JApcr503 (SEQ ID NO. 1) and JApcr502 (cgacggatccttatgttatgtcaaaccaattccac) (SEQ ID NO. 3) to amplify sequences from pCMV/HXB-2.env. The amplified fragments were digested with XbaI and BamHI and subcloned into NheI and BamHI digested JW4303. Western blot analyses of transfected Cos cells revealed sg120 in both the transfected cells and the culture medium.

EXAMPLE 12

Immunogenicity Tests of HIV-1-NL4-3 pBC12CMV Based Vectors

Figure 9:
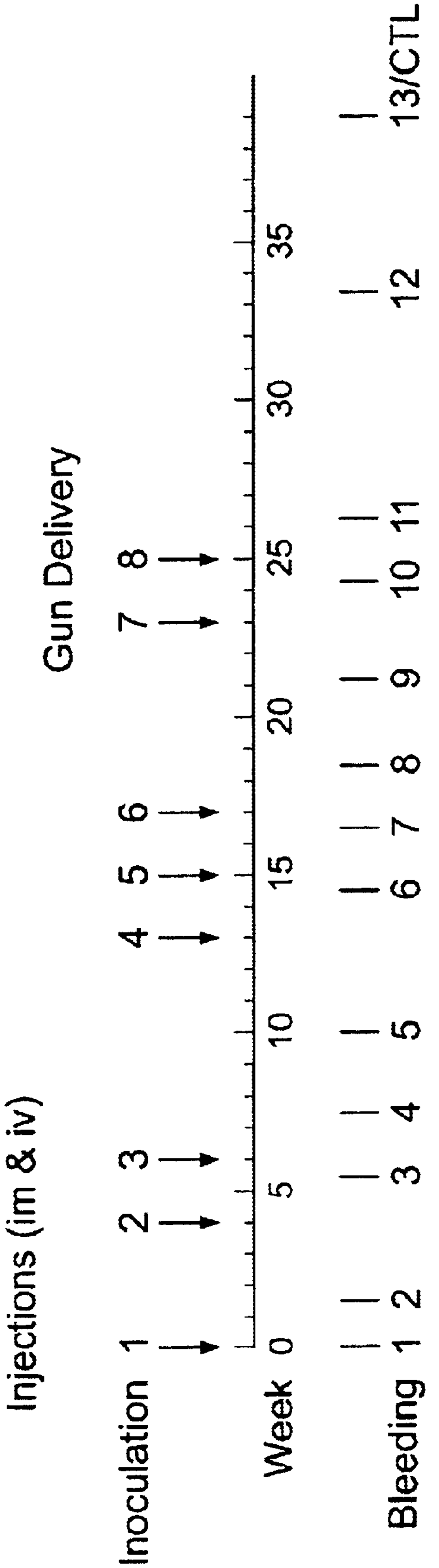
FIG. 9 is a representation of the DNA immunization schedule used in mice for HIV-1 vectors.

A trial immunization with the pBC12/CMV based vectors was conducted in BALB/c mice. Six to 8 week old mice were immunized with a series of injections of 200 μg of DNA administered by both the intravenous (iv) and intramuscular (im) routes (the immunization schedule is shown in FIG. 9). Four experimental groups of six mice received DNA. Group A received pCMV/control DNA without an insert. Group B received pCMV/NL4-3.env DNA. Group C received pCMV/NL4-3.dpol DNA. Group D received a mixture of 100 μg of pCMV/NL4-3.env and 100 μg of pCMV/NL4-3.dpol DNA. Mice were bled prior to immunization and at various times after immunization. At each bleed, sera from the mice present in a test group were pooled. At the end of the experiment, mice were sacrificed and the spleens harvested for assays for cytotoxic T-cell (CTL) activity against a defined CTL epitope in the NL4-3 Env for BALB/c mice.

Levels of anti-Env antibody were scored using enzyme linked immunoadsorbent assays (ELISA). Wells of a microtiter plate were coated with 0.4 μg of purified gp120 per well (purchased from American Biotechnology Inc., Cambridge, Mass.). Mouse sera were pretreated with kaolin to remove non-specific activity (Novak, et al., Vaccine 11:55–60 (1993)). Different dilutions of test sera were incubated in the wells and the amount of anti-gp120 IgG scored using alkaline phosphatase or horse radish peroxidase conjugated goat anti-mouse IgG. Appropriate substrates were added and color development evaluated using an ELISA reader to determine optical densities. Optical density values obtained for sera of the control group (group A) were subtracted from values obtained for experimental groups (groups B,C,D).

Figure 10:
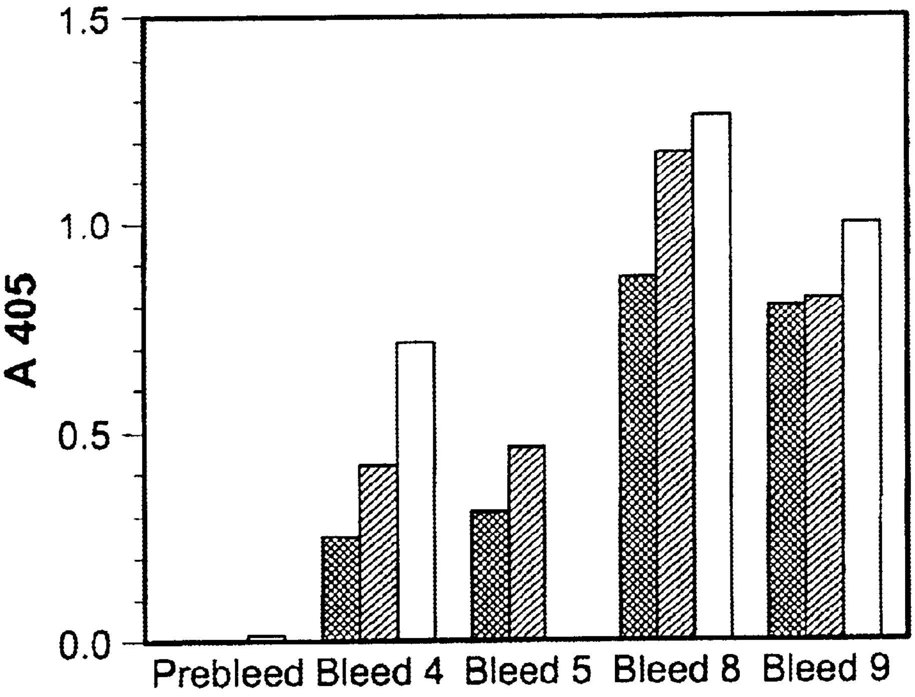
FIG. 10 is a bar graph depicting the levels of anti-gp120 antibody raised in mice by intravenous and intramuscular inoculations. Stippled bars, sera of those receiving NL4-3.env DNA; striped bars, NL4-3.dpol DNA; open bars, both NL4-3.env DNA and NL4-3.dpol DNA.
Figure 11:
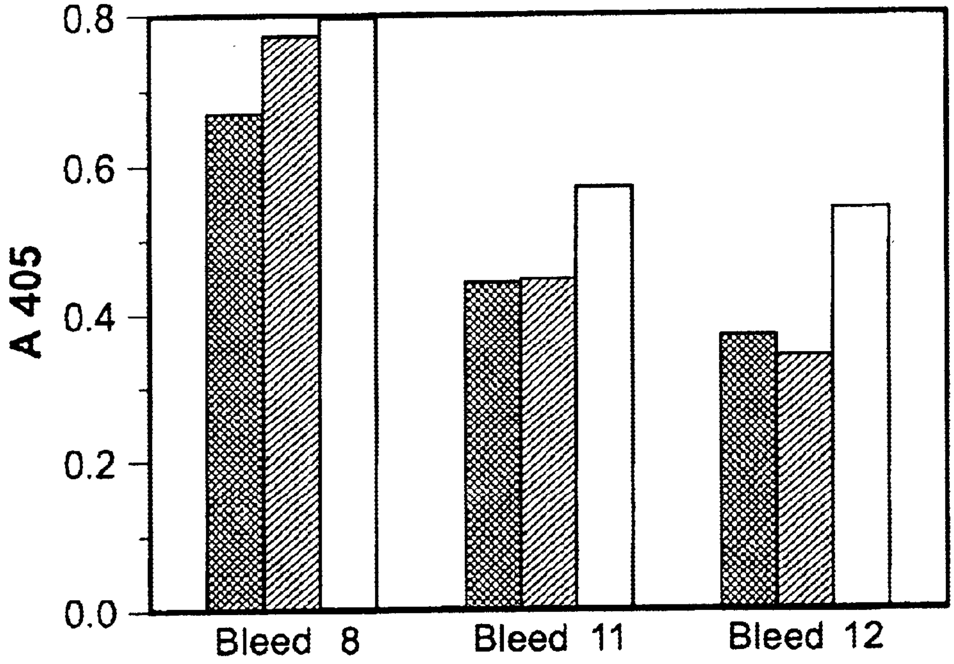
FIG. 11 is a bar graph depicting the levels of anti-gp120 antibody raised in mice by intravenous and intramuscular inoculations, followed by gene gun inoculations. Stippled bars, sera of those receiving NL4-3.env DNA; striped bars, NL4-3.dpol DNA; open bars, both NL4-3.env DNA and NL4-3.dpol DNA.
Figure 12:
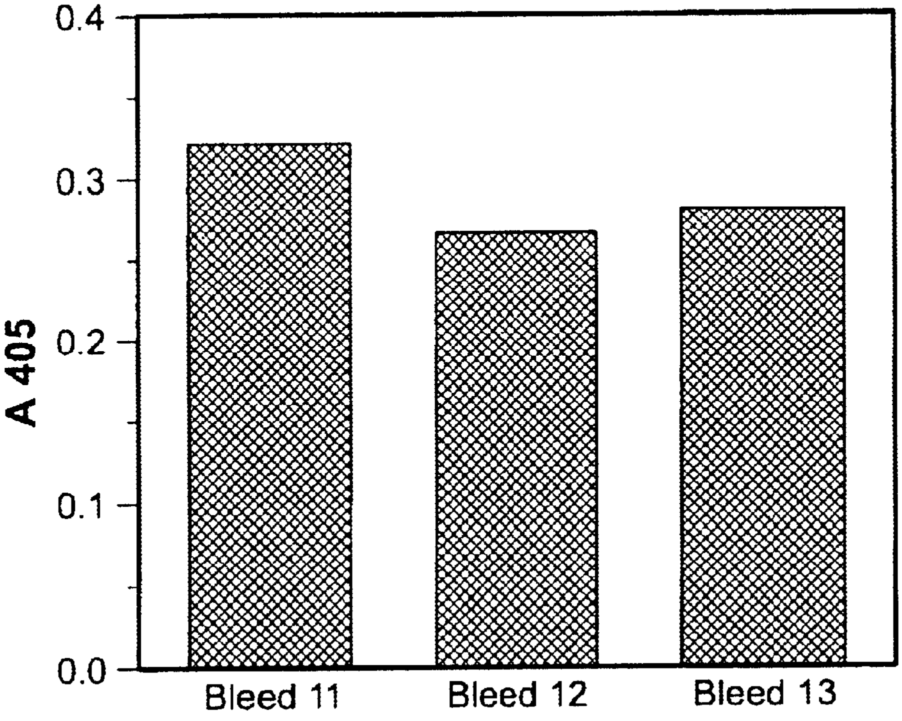
FIG. 12 is a bar graph depicting the longevity of mouse anti-gp120 titer in those animals receiving both NL4-3.env DNA and NL4-3.dpol DNA.
Figure 13:
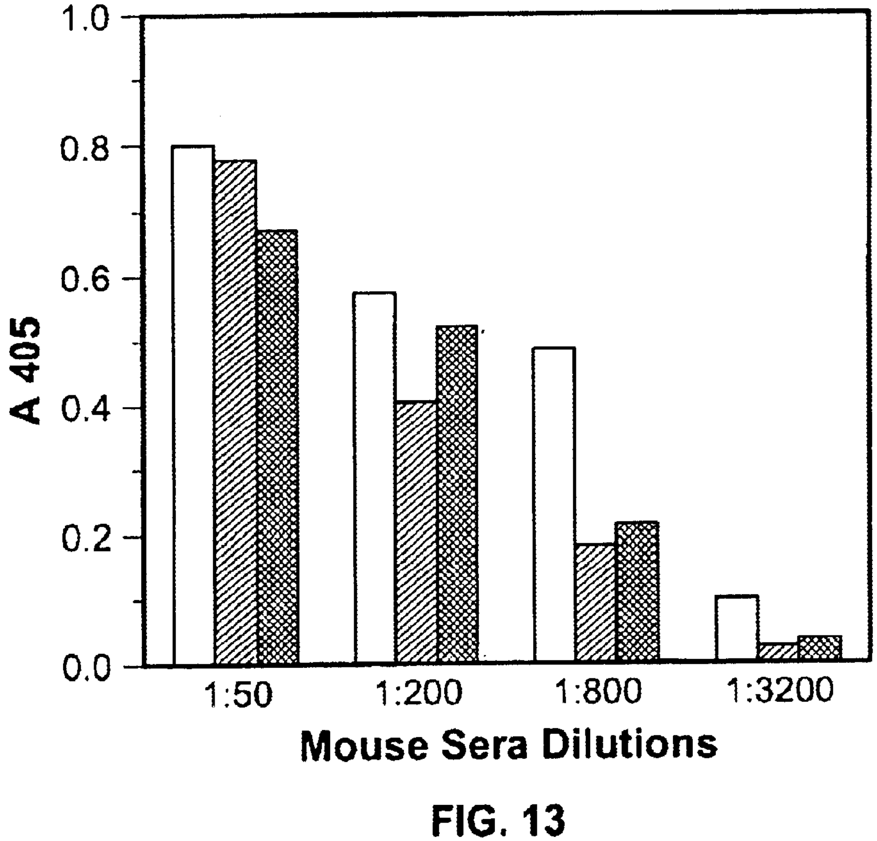
FIG. 13 is a bar graph depicting the titration of anti-gp120 antibody raised in DNA inoculated mice. Stippled bars, sera of those receiving NL4-3.env DNA; striped bars, NL4-3.dpol DNA; open bars, both NL4-3.env DNA and NL4-3.dpol DNA.

The DNA immunizations raised long-lived antibody responses to the HIV-1 envelope (FIGS. 10, 11 and 12). Easily detected levels of anti-Env antibody appeared by bleed 4 (1.5 weeks after the third DNA immunization) (FIG. 10). These levels of antibody persisted, with similar levels of antibody present at bleed 5 (4 weeks post the third DNA incubation) (FIG. 10). The clustered DNA immunizations 4, 5 and 6 substantially raised the titer of anti-Env antibody (see bleed 8 at 1.5 weeks after immunizations 4, 5 and 6) (FIG. 10). These higher levels of antibody persisted, exhibiting only a slow decline with time. Two gene gun inoculations to the abdominal epidermis of 0.4 μg DNA per each of two shots did not increase the titer of anti-Env antibody (FIG. 11). Experimental animals were maintained for an additional 14 weeks after the gene gun inoculations. During this time good titers of anti-Env antibody persisted (FIG. 12).

pCMV/NL4–3,env DNA, pCMV/NL4-3.dpol DNA and the mixture pCMV/NL4-3.env and pCMV/NL4-3.dpol DNA had overall similar abilities to raise antibody (FIG. 10). For each of these DNAS, sera with the highest levels of anti-Env antibody were obtained at bleed 8 (FIGS. 10 and 11). Each of these sera had end point liters of about 1:3200 (FIG. 13). The mixture of dpol and env DNA raised the highest liters of anti-Env IgG (FIGS. 10, 11 and 13). However, these higher titers were less than 4-fold different from those raised by the DNAs given as single species (FIG. 13).

Figure 14:
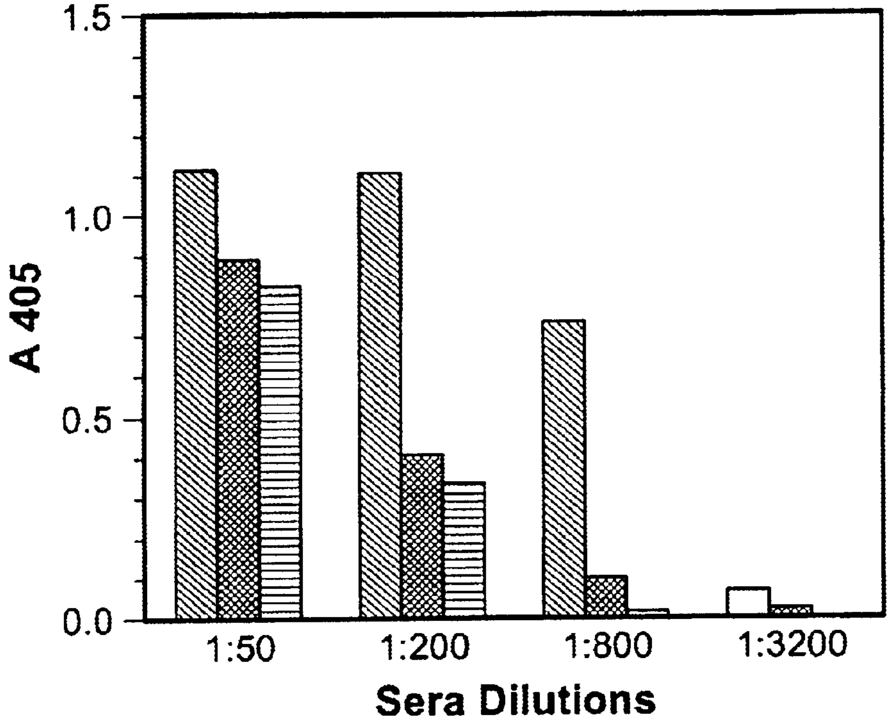
FIG. 14 is a bar graph depicting levels of anti-env antibody raised in mice by gene gun env DNA inoculations. Light filled bars, results from a high responder mouse inoculated only by gene gun; striped bars, results from a moderate responder mouse inoculated only by gene gun; dark filled bars, results from a mouse inoculated by intravenous and intramuscular routes, with NL4-3.env, leed 8.

The levels of anti-Env ELISA antibody raised by the multiple DNA inoculations in saline and a gene gun boost were compared to those obtained by Joel Haynes at Agracetus, Inc. (Middleton, Wis.) using only gene gun delivery of an Env-expressing DNA (FIG. 14). The levels present in the pooled sera from bleed 8 for NL4-3.env inoculated mice from the experiment in FIG. 9 were intermediate between those found in the sera of a high responder mouse and a moderate responder mouse receiving only gene gun DNA. This was consistent with the sera that had been pooled from test groups in the experiment showin in FIG. 9 representing sera with titers much like those raised by three gene-gun deliveries of 0.4 μg DNA to the abdominal epidermis.

Sera from mice were also examined for neutralizing activity to NL4-3. These tests were conducted by incubating 50 to 100 infectious units of NL4-3 with various dilutions of mouse sera that had been heat inactivated and Kaolin treated. Incubations were conducted for one hour at 37° C. Following the incubation, exponentially growing H9 cells were added. 24 hours later, the cells were washed and fed with fresh medium. At four days the cultures were lysed with Triton-X100 and analyzed for the replication of NL4-3 using an antigen capture ELISA. The results of three such assays are summarized in Table 15. The data in Table 15 are the reciprocals of the last dilution of sera giving ≧90% inhibition of NL4-3 replication. HIV-Ig is pooled immunoglobulin from sero-positive humans obtained from the AIDS repository, Bethesda, Md.

TABLE 15

| Titer of Neutralizing Antibody for NL4-3 in DNA-Raised Sera | | | | | |
|---|---|---|---|---|---|
| Animal # | Control | Bleeds 7, 8, 9 | Bleed 11 | Bleed 13 | HIV-Ig |
| 313 | 1:40 | >1:1000 | | | |
| 322 | 1:80 | 1:5120 | 1:5120 | 1:5120 | |
| 324 | <1:100 | 1:6400 | 1:6400 | 1:1600 | 1:100 |

The neutralization tests revealed excellent neutralizing activity in the DNA-immunized mice. In agreement with the ELISA data, mice immunized with N4L4-3.env and NL4-3.dpol DNA had comparable titers of neutralizing antibody. Also in agreement with the ELISA data, the neutralizing antibody exhibited excellent persistence, undergoing $\leqq$ a four fold drop in the 14 weeks following the last DNA inoculation. Thus the DNA inoculations had raised outstanding neutralizing activity against NL4-3. This reflects the presentation of native forms of HIV-1 Env by DNA-expressing cells.

Tests for cytotoxic T-cell (CTL) activity were carried out by Dr. Joel Haynes, Agracetus, Inc. For CTL analyses, mice were sacrificed and responder splenocytes harvested and resuspended in RPMI 1640, 10% fetal calf serum, 50 $\mu$g/ml gentamicin (RPMI-10) containing 10 units of rat interleukin-2 per ml. Stimulator splenocytes were prepared by suspending splenocytes from naive animals in RPMI-10 at a concentration of $1\times10^7$ cells per ml and adding mitomycin C to a final concentration of 25 $\mu$g per ml. Stimulator cells were incubated in the presence of mitomycin C for 25 minutes at 37° C., washed with RPMI-10, and then pulsed with a synthetic peptide representing a known CTL epitope recognized by BALB/c mice (RIQRGPGRAFVTIGK) (SEQ ID NO. 4). Roughly equal numbers of stimulator and responder cells were cocultured for 5 to 6 days. A cytotoxicity assay was employed to measure the ability of the in vitro stimulated responder cells to lyse chromium$^{51}$ loaded peptide pulsed BALB/c 3T3 target cells.

Figure 15:
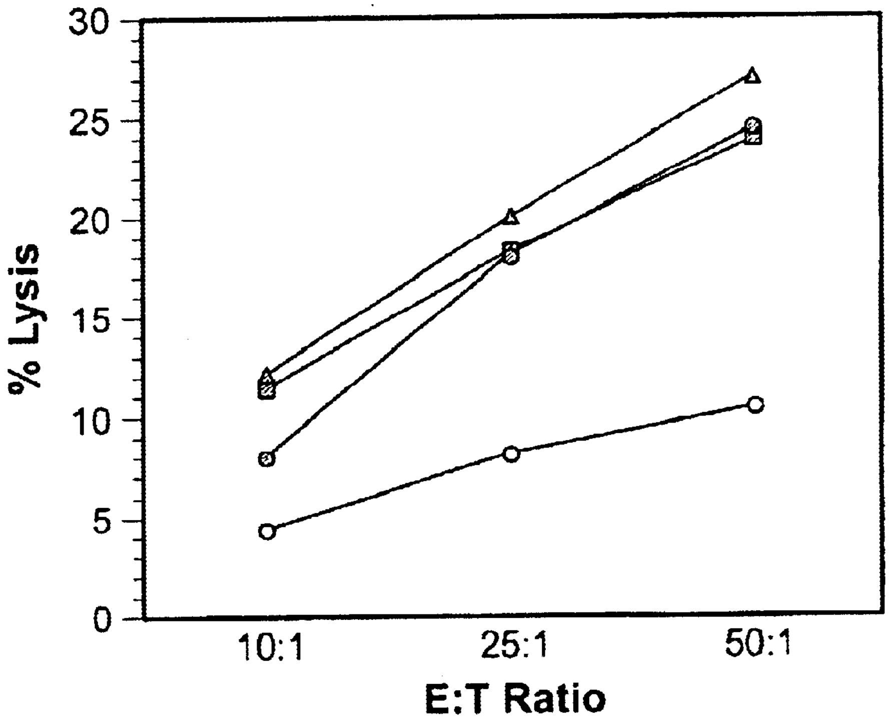
FIG. 15 is a graph depicting the cytotoxic T-cell ctivity of HIV-1 inoculated mice. Open circles, results from mice inoculated with vector; closed circles, NL4-3.env DNA; closed triangles, NL4-3.dpol DNA; closed squares, both NL4-3.env DNA and NL4-3.dpol DNA. E:T=effector to target ratio.

The DNA immunizations raised cytotoxic T-cell activity that was readily detected at the termination of the experiment (14 weeks after the last DNA immunization) (FIG. 15). CTL activities for Env peptide-pulsed target cells were similar for mice immunized with pCMV/NLA-3.env DNA, pCMV/NL4-3.dpol DNA and the mix of pCMV/NLA-3.env and pCMV/NL4-3.dpol DNA.

EXAMPLE 13

DNA Constructs for Immunization Against $SIV_{mac}$

SIV Constructs

As with HIV-1, two series of DNA transcription units have been prepared for immunizations against $SIV_{mac}$. The first of these uses the pBC12/CMV vector of Dr. Bryan R. Cullen (see above and FIG. 4B). The second series used the JW4303 vectors developed at James I. Mullins laboratory (See above and FIG. 6).

pBC12/CMV Based SIV Vectors

Figure 16A:
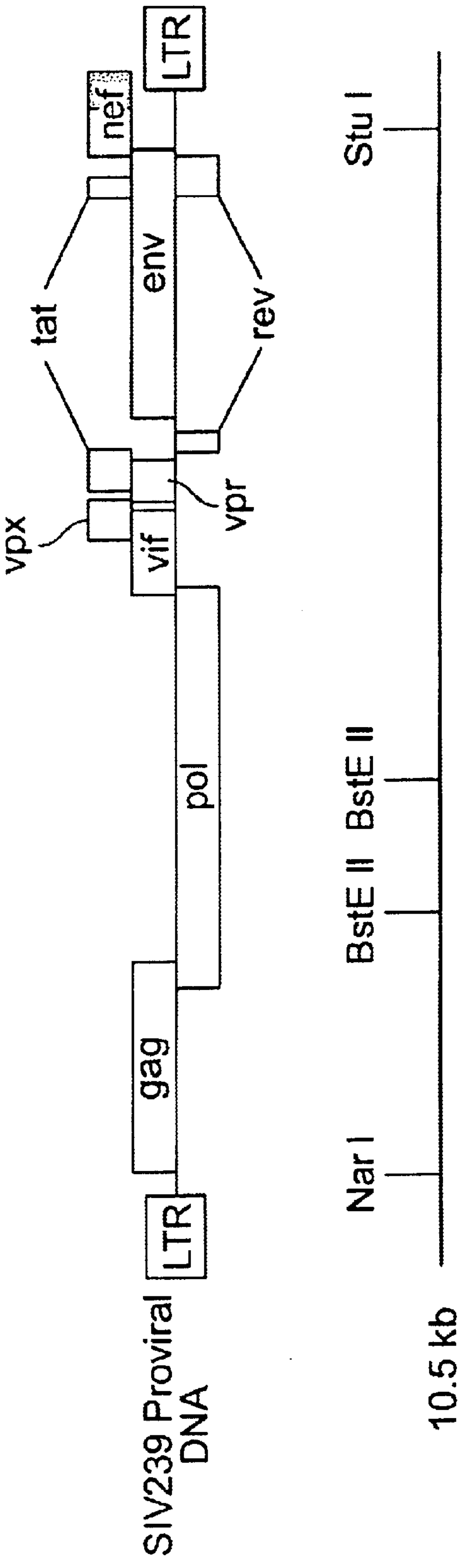
FIG. 16A is a schematic representation of SIV-239 proviral DNA.
Figure 16B:
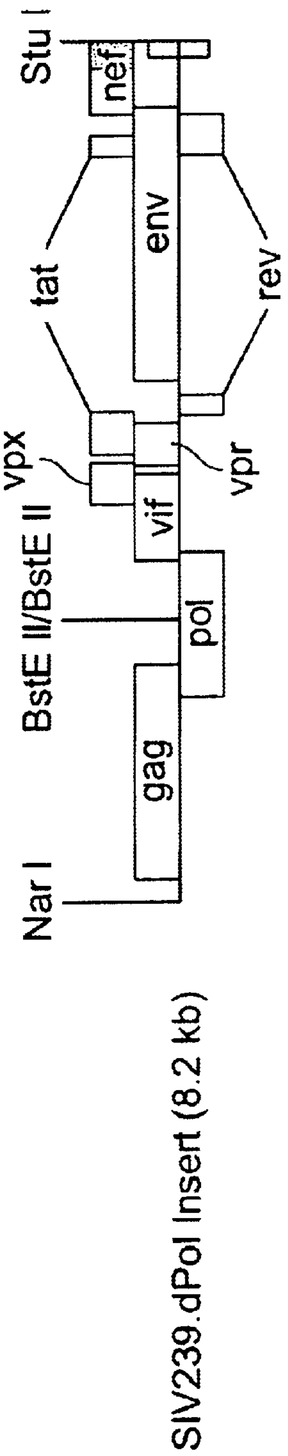
FIG. 16B is a schematic representation of the SIV239.dpol insert.

Cloning into the pBC12/CMV based vectors was performed in pBC12/CMV/IL-2. SIV239 inserts were prepared from plasmids encoding SIV239 proviral DNA (FIG. 16A). These plasmids (p239SpSp5' and p239SpE3') were provided by Dr. Ronald C. Desrosiers, New England Regional Primate Research Center (Southborough, Mass.). Specifically a pCMV/SIV239.dpol (239.dpol) insert (FIG. 16B) was substituted for the BamHI to HindIII fragment of IL-2 cDNA in pBC12/CMV/IL-2. The 239.dpol insert was constructed by rendering the 5' LTR non-functional by a NarI deletion, rendering pol nonfunctional by an internal BstEII deletion, and removing most of the LTR with a StuI digestion. p239SpE3' encodes a defective nef gene, indicated by the stipple. Western blot analyses of transfected Cos cells were used to demonstrate the expression of Gag and Env. Gag and Env proteins were present both in cells and in culture medium. This was anticipated because Gag is the only SIV-1 protein required for particle formation.

JW4303 Based Vectors

The JW4303 DNA transcription units for SIV were constructed using PCR amplified fragments of SIV env sequences (FIGS. 17A–17D). A 5' sense primer supported construction of a DNA encoding a fusion protein with the TPA leader. 3' antisense oligonucleotides were used to create a sgp120, a sgp140 and full length SIV env fragments.

Figures 17A, 17B, 17C, 17D:
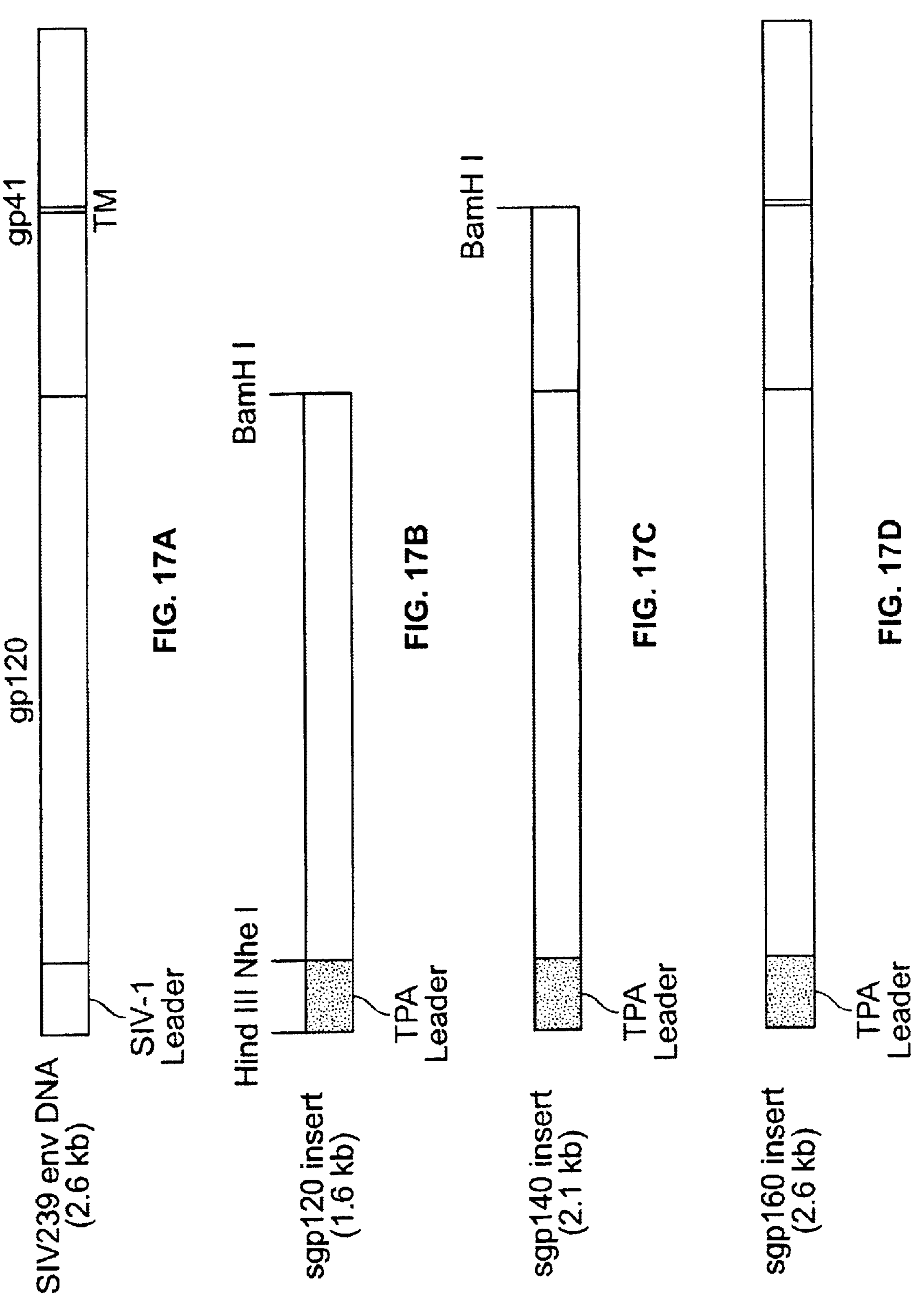
FIG. 17A is a schematic representation of SIV-239.env DNA.
FIG. 17B is a schematic representation of a SIV sgp120 insert.
FIG. 17C is a schematic representation of a SIV sgp140 insert.
FIG. 17D is a schematic representation of a SIV sgp160 insert.
Figure 18:
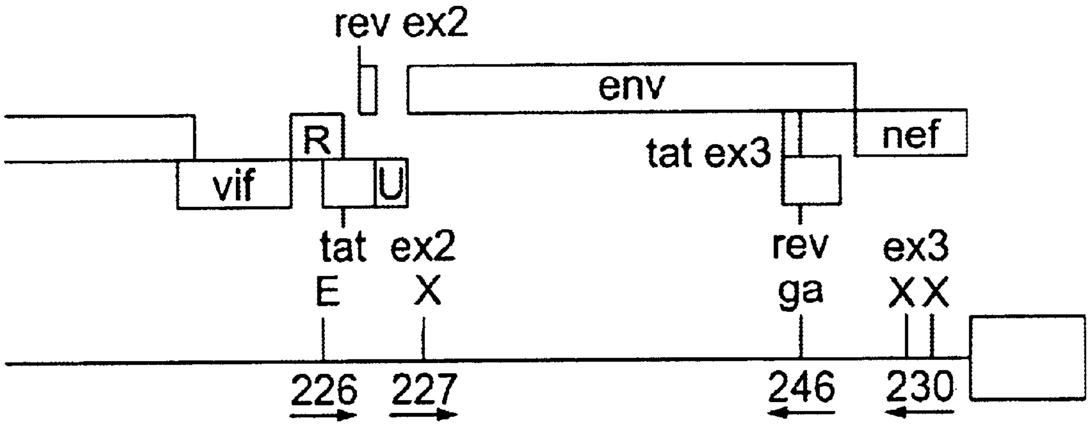
FIG. 18 is a schematic representation of the restriction sites and oligonucleotides used for PCR amplification and subcloning of envs from patient isolates of HIV-1.

JW4303/SIV239.sqp120 (239.sqp120) (FIG. 17B)

239.sgp120 was synthesized using oligonucleotide JApcr19 and oligonucleotide JWpcr8 to amplify sequences from p239spE3'. The amplified fragments were digested with NheI and BamHI and subcloned into NheI and BamHI digested pJW4303. Western blot analyses of transfected Cos cells revealed sg120 in both the transfected cells and the culture medium. 239 sequences were used in this construct because SIV 239 represents an established model for vaccine trials in macaques. SIV 239 is a mutant form of SIV 251, which is also used to generate constructs (see below). The Genbank accession numbers for strain SIV239 are M33262, M61062, and M61093. The Genbank accession numbers for strain SIV251 are M19499 and X06393.

pJW4303/SIV239.sgp140 (239.sgp140) (FIG. 17C)

239.sgp140 was constructed using oligonucleotides JApcr19 and HKpcr2 to amplify sequences from p239SpE3'. The amplified fragments were digested with Nhel and BamHI and subcloned into NheI and BamHI digests pJW4303. Western blot analyses of transfected Cos cells revealed sg140 in both the transfected cells and the culture medium. As indicated above, 239 sequences were used because the 239 virus is established as a model for vaccine trials in macaques.

pJW4303/SIV251.sgp140 (251.sgp140) (FIG. 17C)

251.sgp140 was constructed using oligonucleotides Japcr19 and Hkpcr2 to amplify sequences from pM40KSIV251env (obtained from Dr. Ronald C. Desrosiers, New England Primate Research Center, Southborough, Mass.). The amplified fragments were digested with NheI and BamHI and subcloned into NheI and BamHI digests JW4303. Western blot analyses of transfected Cos cells revealed sgp140 in both the transfected cells and the culture medium.

pJW4303/SIV316.sqp140 (316.sqp140) (FIG. 17C)

316.sgp140 was constructed using oligonucleotides Japcr19 and Hkpcr2 to amplify sequences from PCR env clone 316–3 obtained from Dr. Ronald C. Desrosiers, New England Primate Research Center. The amplified fragments were digested with NheI and BamHI and subcloned into NheI and BamHI digested pJW4303. Western blot analyses of transfected Cos cells revealed sg120 in both the transfected cells and the culture medium. SIV 316 is a mutant form of SIV 239 which has a monocyte/macrophage tropism, (Mori, K. et al., *J. Virology* 66(4):2067–2075 (1992)).

EXAMPLE 14

SIV DNA Vaccine Trial Design

A vaccine trial was undertaken using SIV-encoding DNAs to immunize Rhesus macaques. Young male and female immunocompetent animals are used in the trials. Three clusters of DNA inoculations are given at 1 and 3, 11 and 13, and 21 and 23 weeks of the trial. A lethal challenge is administered two weeks after the final DNA inoculation. This challenge consists of 10 monkey infectious units of SIV239 administered by intravenous inoculation.

Three groups of monkeys have been placed in the trial. Each group is receiving three different SIV239 DNAs: 239.dpol, 239.sgp120, and 239.sgp140 (FIGS. 16D, 17B and 17*c*). At each DNA inoculation, the first group of four macaques is receiving 500 $\mu$g of each of these DNAs by both iv and im routes of inoculation as well as 2 gene gun shots (Accell Instrument) of each of the three DNAs to the thigh skin and two gun shots of each of the three DNAs to the abdominal skin. The second group of monkeys is receiving two gene gun shots of each of the three DNAs to thigh skin and two gun shots of each of the DNAs to abdominal skin. The third group is receiving 500 $\mu$g of the pCMV/control DNA and 1 mg of the pJW4303 DNA by both intravenous and intramuscular routes of inoculation as well as two gene gun shots of the pCMV/control and four gun shots of the pJW4303 DNA administered to the thigh skin and two gene gun shots of the pCMV/control and four gun shots of the pJW4303 DNA administered to abdominal skin.

Gene gun shots of 239.dpol have been accomplished with beads loaded with equimolar amounts of DNA transcriptional unit for $SIV_{mac}$ Rev and 239.dpol. The expression of additional Rev in skin cells increases the level of Gag and Env expression. The transcriptional unit for $SIV_{mac}$ Rev was obtained from Dr. Gregory A. Viglianti, University of Massachusetts Medical Center, Worcester, Mass.

Additional Env-encoding DNAs are added to the vaccine for inoculation at weeks 11 and 13 and 21 and 23. These are added to broaden the immune response to include responses against SIV mutants that arise in infected animals. To accomplish the broadening of the response, the two vaccine groups of monkeys (groups one and two above) receive two gene gun shots of 251.sgp140 and two genegun shots of 316.sgp140. These are delivered to the abdominal epidermis. These shots are given in addition to the same shots received at weeks one and three of the trial.

EXAMPLE 15

Molecular Cloning of HIV-1 env Sequences from Patient Isolates for Use in Vaccine Transcription Units To obtain env sequences for subgroup B HIV-1 isolates representing the slow/low, non-syncytium inducing, monocyte/macrophage tropic viruses characteristic of the healthy seropositive phase of infection as well as env sequences representing the rapid/high, syncytium inducing T-cell line tropic viruses found in patients with AIDS, two series of serial patient isolates were obtained from Dr. Eva Maria Fenyo, Karolinska Institute, Sweden (Von Gegerfelt, A. et al., *Virol.* 185: 162–168 (1991)) (see Table 16). These isolates were obtained over a two to three year period of time during the progression from the healthy, sero-positive phase, to the AIDS phase of infection. One series was from patient 5, and the second from patient 6.

TABLE 16

Designations and Biological Characteristics of Patient Isolates to be Used as a Source of Vaccine DNAs

| Isolate | CD4+ cells/$\mu$l | Replication in PBLs | Cell lines | Syncytium Formation | Susceptibility to Neutralization homologous | Susceptibility to Neutralization heterologous |
|---|---|---|---|---|---|---|
| 5A | 487 | slow | no | – | | |
| 5B | 226 | rapid | yes | +++ | B+, C+ | 1+, 2+ |
| 5C | 100 | rapid | yes | +++ | B–, C– | 1+, 2– |
| 6A | 370 | slow | no | – | | |
| 6B | 470 | slow | no | –/+ | | |
| 6C | 450 | slow | tran* | ++ | A+, B–, C+, D+ | 1+, 2+ |
| 6D | 197 | rapid | yes | +++ | A–, B–, C–, D– | 1–, 2+ |

*tran = transitory. Sera and isolates harvested at the same time are indicated by the same letters. For example, isolate 5B was obtained at the same time as serum B from patient 5. Heterologous sera represent sera from two patients with good neutralizing activity.

Envelope sequences from the isolates have been recovered by polymerase chain reaction (PCR) amplification. Culture supernatants were grown once on mitogen stimulated PBLs. DNA was prepared at five days post infection when high levels of syncytia had appeared for the more virulent isolates. A nested PCR amplification was then used to recover a KpnI to BamIII fragment of env with molecular weight of approximately 2.1 kb. This fragment encodes essentially all of gp120, lacking codons for only the 13 N-terminal amino acids of gp120. It also encodes approximately 240 of the approximately 340 amino acids of gp41, including all of the extracellular and transmembrane domains of gp41 as well as the portion of the intracellular domain that includes a highly acidic sequence.

Oligonucleotide primers for PCR reactions were chosen to include conserved restriction endonuclease sites as well as to maximize the number of 3' bases that are completely conserved among the current HIV-1 isolates in Myers data base (Myers et al., Human Retrovirus and AIDS, Los Alamos National Laboratory, Los Alamos, N.Mex., 1992). Actual amplifications have used 250 ng of DNA, 25 pmole of each primer, and one unit of Amplitaq in a final volume of 100 $\mu$l.

Clones are cloned into a right hand half of pNL4-3 provided by Dr. Ronald C. Desrosiers, New England Primate Research Center, Southborough, Mass.). This is performed as a threepiece cloning of (i) a 2.1 kb KpnI to BamHI fragment of PCR amplified env sequences; (ii) a 0.6 kb EcoRI to KpnI fragment from pNL4-3 (3' vpr to 5' env sequences); and (iii) the EcoRI to BamHI framgnet of the right half of pNL4-3 (contining 3' env, nef, LTR and plasmid sequences). As clones are obtained, a preliminary V3 loop sequence is obtained (see Table 17). This sequence verifies that the clones are not a contaminant and provides a signature sequence for monitoring further subcloning.

TABLE 17 env Clones from Serial Isolates from Patients 5 and 6, and Preliminary V3 Loop Sequence

| Isolate | Clone | pNL4-3/ env | V3 Loop | SEQ ID NO. |
|---|---|---|---|---|
| 5A | EMF | | CTRPNYTTRKRIHIGPGRAFYTTKNIIGNIKQAH | 5 |
| 5B | 4B-2 | p5B-1 | CTRPNYKTRSRIHIGPGRAFYTTKNIRGDIRQAHC | 6 |
| | EMF | | CTRPNYKTRSRIHIGPGR | 7 |
| 5C | EMF | | CTRPNYKTSRRIHIGPGRSFYT | 8 |
| 6A | 4A-27 | p6A-1 | CTRPNNNTRKSIHIGPGRAIYTTGQIIGDIRQAHC | 9 |
| | EMF | | CTRPNNNTRKSIHIGPGRAIYTT | 10 |
| 6B | EMF | | CTRPNNNTRKSIHIGPGRAFYTT?AIIGDIR | 11 |
| 6C | A4-2 | | CTRPNNNTRRRIHIGPGRAIYTTGQIIGDIRQAHC | 12 |
| | A4-4 | | CTRPNNNTRRRIHIGPGRAIYTTGQIIGDIRQAHC | 13 |
| | A4-5 | | CTRPNNNTRRRIHIGPGRAIYTTGQIIGDIRQAHC | 14 |
| | 4C-1 | p6C-1 | | |
| | EMF | | CTRPNNNTRRRIHIGPGRA | 15 |
| 6D | 4A-64 | | CTRPNNNTRRRIHIGPGRAIYTTGQIIGDIRQAHC | 16 |
| | 4D-6 | p6D-1 | CTRPNNNTRRRIHIGPGRAIYTTGQIIGDIRQAHC | 17 |
| | EMF | | CTRPNNNTRRRIHIGPGRA | 18 |
| Consensus B | | | CTRPNNNTRKSIHIGPGRAFYTTGEIIGDIRQAHC | 19 |

EMF = Fenyo lab.

Clones are then tested for biological activity by co-transfection with the left half of pNL4-3 into COS-1 cells and co-cultivation with mitogen stimulated PBLs. The p6B-1, p6A-1, p6C-1 and p6D-1 NL4-3.env recombinants encode functional envs that support the growth characteristics of the stocks from which they were recovered. These envs represent different stages of disease and different growth characteristics of patient isolates. The envs are moved on PCR amplified fragments into the pJW4030 vector for immunogenicity tests (see above, FIGS. 8A–8D).

Equivalents

Those skilled in the art will recognize, or be able to ascertain, using no more than routine experimentation, many equivalents to the specific embodiments of the invention described herein. These and all other such equivalents are intended to be encompassed by the following claims.

What is claimed is:

1. A composition comprising a DNA transcription unit and a physiologically acceptable carrier, wherein the DNA transcription unit comprises DNA encoding an antigen of human immunodeficiency virus operatively linked to a promoter region, and wherein the DNA transcription unit comprises a construct selected from the group consisting of: pCMV/HIV-1-NL4-3.dpol, pCMV/HIV-1-HXB-2.env, pCMV/HIV-NL4-3.env, JW4303/HIV-1-HXB-2.sgp120, and JW4303/HIV-1-HXB-2.sgp140.

2. The composition of claim 1, further comprising one or more additional DNA transcription units, each DNA transcription unit comprising DNA encoding an antigen of a different subgroup of the human immunodeficiency virus.

3. The composition of claim 1, further comprising one or more additional DNA transcription units, each DNA transcription unit comprising DNA encoding an antigen of a different subtype of the human immunodeficiency virus.

4. A composition comprising more than one DNA transcription unit and a physiologically acceptable carrier, wherein each DNA transcription unit comprises DNA encoding an antigen of human immunodeficiency virus operatively linked to a promoter region, and wherein at least one of the DNA transcription units comprises a construct selected from the group consisting of: pCMV/HIV-1-NL4-3.dpol, pCMV/HIV-1-HXB-2.env, pCMV/HIV-NL4-3.env, JW4303/HIV-1-HXB-2.spp120, and JW4303/HIV-1-HXB-2.sgp140.

5. The composition of claim 4, wherein each DNA transcription units comprises DNA encoding an antigen of Env protein from a different subgroup of human immunodeficiency virus.

6. The composition of claim 5, wherein each DNA transcription unit comprises DNA encoding an antigen of Env protein from a different tissue tropism of human immunodeficiency virus.

7. The composition of claim 4, wherein the DNA transcription unit comprises DNA encoding eight of the nine human immunodeficiency virus proteins.

8. A plasmid vector comprising a promoter region operably linked to a nucleotide sequence encoding an antigen of human immunodeficiency virus, wherein said vector comprises a construct selected from the group consisting of: pCMV/HIV-1-NL4-3.dpol, pCMV/HIV-1-HXB-2.env, pCMV/HIV-NL4-3.env, JW4303/HIV-1-HXB-2.sgp120, and JW4303/HIV-1-HXB-2.sgp140, and wherein said antigen of human immunodeficiency virus is expressed in a cell of a mammal inoculated with said plasmid vector.

9. The plasmid vector of claim 8, wherein said antigen of human immunodeficiency virus is Env protein.

10. The plasmid vector of claim 8, wherein said antigen of human immunodeficiency virus includes eight of the nine human immunodeficiency virus proteins.

* * * * *